US011183292B2

(12) United States Patent
Stalling et al.

(10) Patent No.: US 11,183,292 B2
(45) Date of Patent: Nov. 23, 2021

(54) METHOD AND SYSTEM FOR RULE-BASED ANONYMIZED DISPLAY AND DATA EXPORT

(71) Applicant: PME IP PTY LTD, Richmond (AU)

(72) Inventors: Detlev Stalling, Berlin (DE); Malte Westerhoff, Berlin (DE)

(73) Assignee: PME IP PTY LTD, Richmond (AU)

( * ) Notice: Subject to any disclaimer, the term of this patent is extended or adjusted under 35 U.S.C. 154(b) by 703 days.

(21) Appl. No.: 15/220,329

(22) Filed: Jul. 26, 2016

(65) Prior Publication Data

US 2016/0342738 A1  Nov. 24, 2016

Related U.S. Application Data

(63) Continuation-in-part of application No. 14/611,163, filed on Jan. 30, 2015, now Pat. No. 9,524,577, which
(Continued)

(51) Int. Cl.
  *G16H 30/20* (2018.01)
  *G16H 10/60* (2018.01)
  *G16H 15/00* (2018.01)

(52) U.S. Cl.
  CPC ............. *G16H 30/20* (2018.01); *G16H 10/60* (2018.01); *G16H 15/00* (2018.01)

(58) Field of Classification Search
  CPC ....... G06F 19/321; G16H 10/16; G16H 15/00
(Continued)

(56) References Cited

U.S. PATENT DOCUMENTS 2,658,310 A  11/1953  Cook
3,431,200 A   3/1969  Davis
(Continued)

FOREIGN PATENT DOCUMENTS

EP      2405344      1/2012
WO  WO2015063188    5/2015

OTHER PUBLICATIONS

"If hashing is one way, why can we decrypt MD5 hashes?" Security.Stackexchange.com, [online], Published Jun. 28, 2013, available at: < https://security.stackexchange.com/questions/38141/if-hashing-is-one-way-why-can-we-decrypt-md5-hashes > (Year: 2013).*

(Continued)

*Primary Examiner* — Richard W. Crandall
(74) *Attorney, Agent, or Firm* — Sci-Law Strategies, PC

(57) ABSTRACT

The invention provides, in some aspects, a system for implementing a rule derived basis to display anonymized image sets. In various embodiments of the invention, users with the appropriate permission can launch a function inside a system in order to anonymize and export the currently loaded study or studies, or one or more studies identified by a search criteria. The data from the studies that were identified is then anonymized on the system using pre-defined rules. In an embodiment of the present invention, the data from selected studies is anonymized on a server, and only then transmitted to another network device thus minimizing the risk that protected health information can be inadvertently disclosed. In an alternative embodiment of the present invention, the data from selected studies is anonymized on a server, and only the anonymized data is stored to the hard disk or other media of a user viewing the study.

20 Claims, 8 Drawing Sheets

Related U.S. Application Data is a continuation of application No. 13/831,975, filed on Mar. 15, 2013, now Pat. No. 8,976,190.

(60) Provisional application No. 62/199,630, filed on Jul. 31, 2015.

(58) Field of Classification Search
USPC .......................................................... 705/2, 3
See application file for complete search history.

(56) References Cited

U.S. PATENT DOCUMENTS

| | | |
|---|---|---|
| 3,645,040 A | 2/1972 | Ort |
| 4,137,868 A | 2/1979 | Pryor |
| 4,235,043 A | 11/1980 | Harasawa et al. |
| 4,258,661 A | 3/1981 | Margen |
| 4,267,038 A | 5/1981 | Thompson |
| 4,320,594 A | 3/1982 | Raymond |
| 4,746,795 A | 5/1988 | Stewart et al. |
| 4,905,148 A | 2/1990 | Crawford |
| 4,910,912 A | 3/1990 | Lowrey, III |
| 4,928,250 A | 5/1990 | Greenberg et al. |
| 4,958,460 A | 9/1990 | Nielson et al. |
| 4,984,160 A | 1/1991 | Saint Felix et al. |
| 5,031,117 A | 7/1991 | Minor et al. |
| 5,091,960 A | 2/1992 | Butler |
| 5,121,708 A | 6/1992 | Nuttle |
| 5,128,864 A | 7/1992 | Waggener et al. |
| 5,218,534 A | 6/1993 | Trousset et al. |
| 5,235,510 A | 8/1993 | Yamada |
| 5,241,471 A | 8/1993 | Trousset et al. |
| 5,253,171 A | 10/1993 | Hsiao et al. |
| 5,274,759 A | 12/1993 | Yoshioka |
| 5,280,428 A | 1/1994 | Wu et al. |
| 5,287,274 A | 2/1994 | Saint Felix et al. |
| 5,293,313 A | 3/1994 | Cecil |
| 5,307,264 A | 4/1994 | Waggener et al. |
| 5,355,453 A | 10/1994 | Row et al. |
| 5,368,033 A | 11/1994 | Moshfeghi |
| 5,375,156 A | 12/1994 | Kuo-Petravic et al. |
| 5,412,703 A | 5/1995 | Goodenough et al. |
| 5,412,764 A | 5/1995 | Tanaka |
| 5,442,672 A | 8/1995 | Bjorkholm et al. |
| 5,452,416 A | 9/1995 | Hilton |
| 5,488,700 A | 1/1996 | Glassner |
| 5,560,360 A | 10/1996 | Filler |
| 5,594,842 A | 1/1997 | Kaufman et al. |
| 5,602,892 A | 2/1997 | Llacer |
| 5,633,951 A | 5/1997 | Moshfeghi |
| 5,633,999 A | 5/1997 | Clowes et al. |
| 5,640,436 A | 6/1997 | Kawai et al. |
| 5,671,265 A | 9/1997 | Andress |
| 5,744,802 A | 4/1998 | Muehllehner et al. |
| 5,774,519 A | 6/1998 | Lindstrom et al. |
| 5,790,787 A | 8/1998 | Scott et al. |
| 5,793,374 A | 8/1998 | Guenter et al. |
| 5,793,879 A | 8/1998 | Benn et al. |
| 5,813,988 A | 9/1998 | Alfano et al. |
| 5,821,541 A | 10/1998 | Tumer |
| 5,825,842 A | 10/1998 | Taguchi |
| 5,838,756 A | 11/1998 | Taguchi et al. |
| 5,841,140 A | 11/1998 | McCroskey et al. |
| 5,909,476 A | 6/1999 | Cheng et al. |
| 5,930,384 A | 7/1999 | Guillemaud et al. |
| 5,931,789 A | 8/1999 | Alfano et al. |
| 5,950,203 A | 9/1999 | Stakuis |
| 5,960,056 A | 9/1999 | Lai |
| 5,963,612 A | 10/1999 | Navab |
| 5,963,613 A | 10/1999 | Navab |
| 5,963,658 A | 10/1999 | Klibanov et al. |
| 6,002,739 A | 12/1999 | Heumann |
| 6,018,562 A | 1/2000 | Willson |
| 6,032,264 A | 2/2000 | Beffa et al. |
| 6,044,132 A | 3/2000 | Navab |
| 6,049,390 A | 4/2000 | Notredame |
| 6,049,582 A | 4/2000 | Navab |
| 6,072,177 A | 6/2000 | Mccroskey et al. |
| 6,088,423 A | 7/2000 | Krug et al. |
| 6,091,422 A | 7/2000 | Ouaknine et al. |
| 6,104,827 A | 8/2000 | Benn et al. |
| 6,105,029 A | 8/2000 | Maddalozzo, Jr. et al. |
| 6,108,007 A | 8/2000 | Shochet |
| 6,108,576 A | 8/2000 | Alfano et al. |
| 6,123,733 A | 9/2000 | Dalton |
| 6,175,655 B1 | 1/2001 | George |
| 6,205,120 B1 | 3/2001 | Packer et al. |
| 6,219,061 B1 | 4/2001 | Lauer et al. |
| 6,226,005 B1 | 5/2001 | Laferriere |
| 6,236,704 B1 | 5/2001 | Navab et al. |
| 6,243,098 B1 | 6/2001 | Lauer et al. |
| 6,249,594 B1 | 6/2001 | Hibbard |
| 6,255,655 B1 | 7/2001 | McCroskey et al. |
| 6,264,610 B1 | 7/2001 | Zhu |
| 6,268,846 B1 | 7/2001 | Georgiev |
| 6,278,460 B1 | 8/2001 | Myers et al. |
| 6,282,256 B1 | 8/2001 | Grass et al. |
| 6,289,235 B1 | 9/2001 | Webber et al. |
| 6,304,771 B1 | 10/2001 | Yodh et al. |
| 6,320,928 B1 | 11/2001 | Vaillant et al. |
| 6,324,241 B1 | 11/2001 | Besson |
| 6,377,257 B1 | 4/2002 | Borrel |
| 6,377,266 B1 | 4/2002 | Baldwin |
| 6,384,821 B1 | 5/2002 | Borrel |
| 6,404,843 B1 | 6/2002 | Vaillant |
| 6,415,013 B1 | 7/2002 | Hsieh et al. |
| 6,470,067 B1 | 10/2002 | Harding |
| 6,470,070 B2 | 10/2002 | Menhardt |
| 6,473,793 B1 | 10/2002 | Dillon et al. |
| 6,475,150 B2 | 11/2002 | Haddad |
| 6,507,633 B1 | 1/2003 | Elbakri et al. |
| 6,510,241 B1 | 1/2003 | Vaillant et al. |
| 6,519,355 B2 | 2/2003 | Nelson |
| 6,526,305 B1 | 2/2003 | Mori |
| 6,557,102 B1 * | 4/2003 | Wong ..................... G16H 30/20 713/176 |
| 6,559,958 B2 | 5/2003 | Motamed |
| 6,591,004 B1 | 7/2003 | VanEssen et al. |
| 6,615,063 B1 | 9/2003 | Ntziachristos et al. |
| 6,633,688 B1 | 10/2003 | Nixon |
| 6,636,623 B2 | 10/2003 | Nelson et al. |
| 6,654,012 B1 | 11/2003 | Lauer et al. |
| 6,658,142 B1 | 12/2003 | Kam et al. |
| 6,664,963 B1 | 12/2003 | Zatz |
| 6,674,430 B1 | 1/2004 | Kaufman et al. |
| 6,697,508 B2 | 2/2004 | Nelson |
| 6,707,878 B2 | 3/2004 | Claus et al. |
| 6,718,195 B2 | 4/2004 | Van Der Mark et al. |
| 6,731,283 B1 | 5/2004 | Navab |
| 6,740,232 B1 | 5/2004 | Beaulieu |
| 6,741,730 B2 | 5/2004 | Rahn et al. |
| 6,744,253 B2 | 6/2004 | Stolarczyk |
| 6,744,845 B2 | 6/2004 | Harding et al. |
| 6,745,070 B2 | 6/2004 | Wexler et al. |
| 6,747,654 B1 | 6/2004 | Laksono et al. |
| 6,754,299 B2 | 6/2004 | Patch |
| 6,765,981 B2 | 7/2004 | Heumann |
| 6,768,782 B1 | 7/2004 | Hsieh et al. |
| 6,770,893 B2 | 8/2004 | Nelson |
| 6,771,733 B2 | 8/2004 | Katsevich |
| 6,778,127 B2 | 8/2004 | Stolarczyk et al. |
| 6,785,409 B1 | 8/2004 | Suri |
| 6,798,417 B1 | 9/2004 | Taylor |
| 6,807,581 B1 | 10/2004 | Starr et al. |
| 6,825,840 B2 | 11/2004 | Gritz |
| 6,825,843 B2 | 11/2004 | Allen et al. |
| 6,923,906 B2 | 8/2005 | Oswald et al. |
| 6,947,047 B1 | 9/2005 | Moy et al. |
| 6,978,206 B1 | 12/2005 | Pu |
| 7,003,547 B1 | 2/2006 | Hubbard |
| 7,006,101 B1 | 2/2006 | Brown et al. |
| 7,031,022 B1 | 4/2006 | Komori et al. |
| 7,034,828 B1 | 4/2006 | Drebin et al. |
| 7,039,723 B2 | 5/2006 | Hu |
| 7,050,953 B2 | 5/2006 | Chiang et al. |

(56) References Cited

U.S. PATENT DOCUMENTS

| | | |
|---|---|---|
| 7,054,852 B1 | 5/2006 | Cohen |
| 7,058,644 B2 | 6/2006 | Patchet et al. |
| 7,076,735 B2 | 7/2006 | Callegari |
| 7,098,907 B2 | 8/2006 | Houston et al. |
| 7,120,283 B2 | 10/2006 | Thieret |
| 7,133,041 B2 | 11/2006 | Kaufman et al. |
| 7,154,985 B2 | 12/2006 | Dobbs |
| 7,167,176 B2 | 1/2007 | Sloan et al. |
| 7,184,041 B2 | 2/2007 | Heng et al. |
| 7,185,003 B2 | 2/2007 | Bayliss et al. |
| 7,219,085 B2 | 5/2007 | Buck et al. |
| 7,242,401 B2 | 7/2007 | Yang et al. |
| 7,262,770 B2 | 8/2007 | Sloan et al. |
| 7,274,368 B1 | 9/2007 | Keslin |
| 7,299,232 B2 | 11/2007 | Stakutis et al. |
| 7,315,926 B2 | 1/2008 | Fridella et al. |
| 7,324,116 B2 | 1/2008 | Boyd et al. |
| 7,339,585 B2 | 3/2008 | Verstraelen et al. |
| 7,472,156 B2 | 12/2008 | Philbrick et al. |
| 7,502,869 B2 | 3/2009 | Boucher et al. |
| 7,506,375 B2 | 3/2009 | Kanda et al. |
| 7,552,192 B2 | 6/2009 | Carmichael |
| 7,609,884 B1 | 10/2009 | Stalling |
| 7,693,318 B1 | 4/2010 | Stalling |
| 7,701,210 B2 | 4/2010 | Ichinose |
| 7,778,392 B1 | 8/2010 | Bergman |
| 7,876,944 B2 | 1/2011 | Stalling |
| 7,889,895 B2 | 2/2011 | Nowinski |
| 7,899,516 B2 | 3/2011 | Chen et al. |
| 7,907,759 B2 | 3/2011 | Hundley |
| 7,956,612 B2 | 6/2011 | Sorensen |
| 7,983,300 B2 | 7/2011 | Vaughan et al. |
| 7,991,837 B1 | 8/2011 | Tahan |
| 7,995,824 B2 | 8/2011 | Yim |
| 8,107,592 B2 | 1/2012 | Bergman |
| 8,189,002 B1 | 5/2012 | Westerhoff |
| 8,319,781 B2 | 11/2012 | Westerhoff |
| 8,369,600 B2 | 2/2013 | Can et al. |
| 8,386,560 B2 | 2/2013 | Ma |
| 8,392,529 B2 | 3/2013 | Westerhoff |
| 8,508,539 B2 | 8/2013 | Vlietinck |
| 8,538,108 B2 | 9/2013 | Shekhar |
| 8,542,136 B1 | 9/2013 | Owsley et al. |
| 8,548,215 B2 | 10/2013 | Westerhoff |
| 8,775,510 B2 | 7/2014 | Westerhoff |
| 8,976,190 B1 | 3/2015 | Westerhoff |
| 9,019,287 B2 | 4/2015 | Westerhoff |
| 9,167,027 B2 | 10/2015 | Westerhoff |
| 9,299,156 B2 | 3/2016 | Zalis |
| 9,355,616 B2 | 5/2016 | Westerhoff |
| 9,454,813 B2 | 9/2016 | Westerhoff |
| 9,509,802 B1 | 11/2016 | Westerhoff |
| 9,524,577 B1 | 12/2016 | Westerhoff |
| 9,531,789 B2 | 12/2016 | Westerhoff |
| 9,595,242 B1 | 3/2017 | Westerhoff |
| 9,728,165 B1 | 8/2017 | Westerhoff |
| 9,749,245 B2 | 8/2017 | Stalling |
| 9,860,300 B2 | 1/2018 | Westerhoff |
| 9,898,855 B2 | 2/2018 | Westerhoff |
| 9,904,969 B1 | 2/2018 | Westerhoff |
| 9,984,460 B2 | 5/2018 | Westerhoff |
| 9,984,478 B2 | 5/2018 | Westerhoff |
| 10,038,739 B2 | 7/2018 | Westerhoff |
| 10,043,482 B2 | 8/2018 | Westerhoff |
| 10,070,839 B2 | 9/2018 | Westerhoff |
| 10,311,541 B2 | 6/2019 | Westerhoff |
| 10,320,684 B2 | 6/2019 | Stalling |
| 10,373,368 B2 | 8/2019 | Westerhoff |
| 10,380,970 B2 | 8/2019 | Westerhoff |
| 10,395,398 B2 | 8/2019 | Westerhoff |
| 10,430,914 B2 | 10/2019 | Westerhoff |
| 10,540,803 B2 | 1/2020 | Westerhoff |
| 10,614,543 B2 | 4/2020 | Westerhoff |
| 10,631,812 B2 | 4/2020 | Westerhoff |
| 10,686,868 B2 | 6/2020 | Westerhoff |
| 10,706,538 B2 | 7/2020 | Westerhoff |
| 2001/0026848 A1 | 10/2001 | Van Der Mark |
| 2002/0004727 A1* | 1/2002 | Knaus ............... G16H 10/60 705/3 |
| 2002/0016813 A1 | 2/2002 | Woods et al. |
| 2002/0034817 A1 | 3/2002 | Henry et al. |
| 2002/0049825 A1 | 4/2002 | Jewett et al. |
| 2002/0080143 A1 | 6/2002 | Morgan et al. |
| 2002/0089587 A1 | 7/2002 | White et al. |
| 2002/0099290 A1 | 7/2002 | Haddad |
| 2002/0099844 A1 | 7/2002 | Baumann et al. |
| 2002/0120727 A1 | 8/2002 | Curley et al. |
| 2002/0123680 A1 | 9/2002 | Vailant |
| 2002/0138019 A1 | 9/2002 | Wexler |
| 2002/0150202 A1 | 10/2002 | Harding |
| 2002/0150285 A1 | 10/2002 | Nelson |
| 2002/0180747 A1 | 12/2002 | Lavelle et al. |
| 2002/0184238 A1 | 12/2002 | Chylla |
| 2002/0184349 A1 | 12/2002 | Maukyan |
| 2003/0001842 A1 | 1/2003 | Munshi |
| 2003/0031352 A1 | 2/2003 | Nelson et al. |
| 2003/0059110 A1 | 3/2003 | Wilt |
| 2003/0065268 A1 | 4/2003 | Chen et al. |
| 2003/0086599 A1 | 5/2003 | Armato |
| 2003/0103666 A1 | 6/2003 | Edie et al. |
| 2003/0120743 A1 | 6/2003 | Coatney et al. |
| 2003/0123720 A1 | 7/2003 | Launav et al. |
| 2003/0149812 A1 | 8/2003 | Schoenthal et al. |
| 2003/0158786 A1 | 8/2003 | Yaron |
| 2003/0176780 A1 | 9/2003 | Arnold |
| 2003/0179197 A1 | 9/2003 | Sloan et al. |
| 2003/0194049 A1 | 10/2003 | Claus et al. |
| 2003/0220569 A1 | 11/2003 | Dione |
| 2003/0220772 A1 | 11/2003 | Chiang et al. |
| 2003/0227456 A1 | 12/2003 | Gritz |
| 2003/0234791 A1 | 12/2003 | Boyd et al. |
| 2004/0010397 A1 | 1/2004 | Barbour et al. |
| 2004/0012596 A1 | 1/2004 | Allen et al. |
| 2004/0015062 A1 | 1/2004 | Ntziachristos et al. |
| 2004/0022348 A1 | 2/2004 | Heumann |
| 2004/0059822 A1 | 3/2004 | Jiang |
| 2004/0066384 A1 | 4/2004 | Ohba |
| 2004/0066385 A1 | 4/2004 | Kilgard |
| 2004/0066891 A1 | 4/2004 | Freytag |
| 2004/0078238 A1* | 4/2004 | Thomas ............... G06F 19/321 705/3 |
| 2004/0102688 A1 | 5/2004 | Walker |
| 2004/0125103 A1 | 7/2004 | Kaufman |
| 2004/0133652 A1 | 7/2004 | Miloushev et al. |
| 2004/0147039 A1 | 7/2004 | Van Der Mark |
| 2004/0162677 A1 | 8/2004 | Bednar |
| 2004/0170302 A1 | 9/2004 | Museth et al. |
| 2004/0210584 A1 | 10/2004 | Nir et al. |
| 2004/0215858 A1 | 10/2004 | Armstrong et al. |
| 2004/0215868 A1 | 10/2004 | Solomon et al. |
| 2004/0239672 A1 | 12/2004 | Schmidt |
| 2004/0240753 A1 | 12/2004 | Hu |
| 2005/0012753 A1 | 1/2005 | Karlov |
| 2005/0017972 A1 | 1/2005 | Poole et al. |
| 2005/0066095 A1 | 3/2005 | Mullick et al. |
| 2005/0088440 A1 | 4/2005 | Sloan et al. |
| 2005/0128195 A1 | 6/2005 | Houston et al. |
| 2005/0152590 A1 | 7/2005 | Thieret |
| 2005/0165623 A1* | 7/2005 | Landi ............... G16H 10/60 705/2 |
| 2005/0225554 A1 | 10/2005 | Bastos et al. |
| 2005/0231503 A1 | 10/2005 | Heng et al. |
| 2005/0239102 A1 | 10/2005 | Berzin |
| 2005/0240628 A1 | 10/2005 | Jiang et al. |
| 2005/0256741 A1* | 11/2005 | Kohan ............... G06Q 10/10 705/2 |
| 2005/0256742 A1* | 11/2005 | Kohan ............... G06F 21/6245 705/2 |
| 2005/0259103 A1 | 11/2005 | Kilgard et al. |
| 2005/0270298 A1 | 12/2005 | Thieret |
| 2005/0271302 A1 | 12/2005 | Khamene et al. |
| 2006/0010438 A1 | 1/2006 | Brady et al. |
| 2006/0010454 A1 | 1/2006 | Napoli et al. |
| 2006/0028479 A1 | 2/2006 | Chun |

(56) References Cited

U.S. PATENT DOCUMENTS

| | | |
|---|---|---|
| 2006/0034511 A1 | 2/2006 | Verstraelen |
| 2006/0066609 A1 | 3/2006 | Iodice |
| 2006/0214949 A1 | 8/2006 | Zhang |
| 2006/0197780 A1 | 9/2006 | Watkins et al. |
| 2006/0229911 A1* | 10/2006 | Gropper .............. G16H 30/20 705/2 |
| 2006/0239540 A1 | 10/2006 | Serra |
| 2006/0239589 A1 | 10/2006 | Omernick |
| 2006/0282253 A1 | 12/2006 | Buswell et al. |
| 2007/0005798 A1 | 1/2007 | Gropper et al. |
| 2007/0038939 A1 | 2/2007 | Challen |
| 2007/0046966 A1 | 3/2007 | Mussack |
| 2007/0067497 A1 | 3/2007 | Craft et al. |
| 2007/0092864 A1 | 4/2007 | Reinhardt |
| 2007/0097133 A1 | 5/2007 | Stauffer et al. |
| 2007/0116332 A1 | 5/2007 | Cai et al. |
| 2007/0127802 A1 | 6/2007 | Odry |
| 2007/0156955 A1 | 7/2007 | Royer, Jr. |
| 2007/0165917 A1 | 7/2007 | Cao et al. |
| 2007/0185879 A1 | 8/2007 | Roublev et al. |
| 2007/0188488 A1 | 8/2007 | Choi |
| 2007/0226314 A1 | 9/2007 | Eick et al. |
| 2007/0255704 A1* | 11/2007 | Baek .............. G06F 21/6254 |
| 2007/0280518 A1 | 12/2007 | Nowinski |
| 2008/0009055 A1 | 1/2008 | Lewnard |
| 2008/0042923 A1 | 2/2008 | De Laet |
| 2008/0086557 A1 | 4/2008 | Roach |
| 2008/0115139 A1 | 5/2008 | Inglett et al. |
| 2008/0137929 A1 | 6/2008 | Chen et al. |
| 2008/0147554 A1 | 6/2008 | Stevens et al. |
| 2008/0155890 A1 | 7/2008 | Oyler |
| 2008/0174593 A1 | 7/2008 | Ham |
| 2008/0208961 A1 | 8/2008 | Kim et al. |
| 2008/0224700 A1 | 9/2008 | Sorensen |
| 2008/0281908 A1 | 11/2008 | McCanne et al. |
| 2008/0317317 A1 | 12/2008 | Shekhar |
| 2009/0005693 A1 | 1/2009 | Brauner et al. |
| 2009/0043988 A1 | 2/2009 | Archer et al. |
| 2009/0077097 A1 | 3/2009 | Lacapra et al. |
| 2009/0147793 A1 | 6/2009 | Hayakawa et al. |
| 2009/0208082 A1 | 8/2009 | Westerhoff et al. |
| 2009/0210487 A1 | 8/2009 | Westerhoff et al. |
| 2009/0225076 A1 | 9/2009 | Vlietinck |
| 2009/0245610 A1 | 10/2009 | Can et al. |
| 2009/0313170 A1* | 12/2009 | Goldner .............. G16Z 99/00 705/50 |
| 2010/0054556 A1 | 3/2010 | Novatzky |
| 2010/0060652 A1 | 3/2010 | Karlsson |
| 2010/0123733 A1 | 5/2010 | Zaharia |
| 2010/0174823 A1 | 7/2010 | Huang |
| 2010/0272342 A1 | 10/2010 | Berman et al. |
| 2010/0278405 A1 | 11/2010 | Kakadiaris et al. |
| 2011/0044524 A1 | 2/2011 | Wang et al. |
| 2011/0112862 A1* | 5/2011 | Yu .............. G06F 16/958 705/3 |
| 2011/0125646 A1* | 5/2011 | Yung .............. G16H 30/20 705/50 |
| 2012/0078088 A1 | 3/2012 | Whitestone et al. |
| 2012/0226916 A1* | 9/2012 | Hahn .............. G06F 16/00 713/193 |
| 2012/0233153 A1 | 9/2012 | Roman et al. |
| 2013/0176319 A1 | 7/2013 | Westerhoff |
| 2013/0195329 A1 | 8/2013 | Canda |
| 2015/0213288 A1 | 7/2015 | Bilodeau et al. |
| 2016/0012181 A1 | 1/2016 | Massey |
| 2017/0011514 A1 | 1/2017 | Westerhoff |
| 2017/0346883 A1 | 3/2017 | Westerhoff |
| 2017/0098329 A1 | 4/2017 | Westerhoff |
| 2017/0104811 A1 | 4/2017 | Westerhoff |
| 2017/0178593 A1 | 6/2017 | Westerhoff |
| 2019/0318512 A1 | 10/2019 | Westerhoff |

OTHER PUBLICATIONS

"Rule," Merriam-Webster.com,[online], accessed Jul. 8, 2019, available at: < https://www.merriam-webster.com/dictionary/rule > (Year: 2019).*

Hunton Andrews Kurth, HHS Publishes Guidance on How to De-Identify Protected Health Information, [online], published on Nov. 27, 2012, available at: < https://www.huntonprivacyblog.com/2012/11/27/hhs-publishes-guidance-on-how-to-de-identify-protected-health-information/ > (Year: 2012).*

PCT/EP2016/067886, Preliminary and International Search Reports, dated Jan. 17, 2017, 18 pages.

Tao, W., Tomographic mammography using a limited number of low dose cone beam projection images, Medical Physics, AIP, Melville, NY vol. 30, pp. 365-380, Mar. 2003, ISSN: 0094-2405.

Wikipedia, Anonymous, 'Volume Rendering' May 30, 2015, retrieved Nov. 4, 2016, https://en.wikipedia.org/w/index.php?title=Volume_rendering&oldid=664765767.

Wikipedia, Anonymous, 'Tomographic Reconstruction' Dec. 6, 2014, retrieved Nov. 4, 2016, https://en.wikipedia.org/w/index.php?title=Tomographic_Reconstruction&oldid=636925688.

PCT/EP2016/067886, Preliminary and International Search Reports, dated Jan. 17, 2017.

https://www.biotechniques.com/bioinformatics-computational-biology/big-data-in-big-trouble/ "Big Data_in_big_trouble?", *BioTechniques*, Sep. 13, 2019.

Re-identification of court decisions by linkage of data banks, Jusletter 2 (2019) by Kerstin Noëlle Volkinger et al.

Jusletter 2 (2019) machine translation of abstract.

Boone et al., Recognition of Chest Radiograph Orientation for Picture Archiving and Communications Systems Display Using Neural Networks, J. Digital Imaging, 1992, 5(3), 190-193.

Boone et al., Automated Recognition of Lateral from PA Chest Radiographs: Saving Seconds in a PACS Environment, J. Digital Imaging, 2003, 16(4), 345-349.

Luo et al., Automatic Image Hanging Protocol for Chest Radiographs in a PACS, IEEE Transactions on Information Technology in Biomedicine, 2006, 10(2), 302-311.

PCT/EP2018/075744, Preliminary and International Search Reports, dated Feb. 1, 2019, 17 pages.

JP2018-524544, Office Action, dated Jun. 2, 2020, 4 pages (& English translation).

EP3329405, Office Action, dated Apr. 6, 2020, 5 pages.

* cited by examiner

Media Exporter

Patient
Name: De-identified
Actual data size: ~14 MB

Options
Destination: Export files to local client folder
Export Folder: /Users/johnson/Media Export [Browse]
Media Folder: 2015-07-26-001
☐ Include Media Viewer  ☐ Autorun Media Viewer  ☐ Uncompressed only (IHE)
☑ De-Identify  [Details...]

Progress
File transfer not started.
[        0%        ]

[Make Default]                                    [Export] [Close]

Figure 3A

De-identification Details

| DICOM Tag | Description | New Value | < | Old Value |
|---|---|---|---|---|
| Patient 1 | | | | |
| 0010-0010 | Patient Name | De-identified | < | SMITH^MARY^F^^ |
| 0010-0020 | Patient ID | f59c4a5c | < | PAT12345 |
| 0010-0030 | Patient Birth Date | 19320101 | < | 19320509 |
| Study 1 | | | | |
| 0008-0050 | Accession Number | 1c457efc | < | EXM5678 |
| 0020-0010 | Study ID | a43ee1b2 | < | EXM5678 |
| 0008-1030 | Study Description | THORAX AP | < | THORAX AP |
| 0032-4000 | Study Comments | | < | |
| 0008-0080 | Institution Name | | < | SPRINGFILDENERAL HOSPITAL |

☑ Remove other demographic tags       ☑ Remove private tags

[ OK ]  [ Cancel ]

List of Auto-Prior Rules

Prior Chest CR

○ System   ● User

[New Rule] [Move to System] [Delete Rule] [Properties...]

Auto-Prior Rule Properties

Name: Prior Chest CR
User Levels:
Comment: For any current chest study CR load prior CT or CR exams of the chest
Other: ☐ Disable   ☐ Overwrite system rule Current study must match all of the following:

| All of the following ◆ |
| Modality ◆ | Contains Any Of ◆ | CR CT | [+][-] |
| Any of the following ◆ | | | [+][-] |
| Body Part Examined ◆ | Equals ◆ | CHEST | [+][-] |
| Study Description ◆ | Contains Any Of ◆ | CHEST THORAX | [+][-] |

Prior study must match all of the following:

| All of the following ◆ |
| Modality ◆ | Contains Any Of ◆ | CR | [+][-] |
| Any of the following ◆ | | | [+][-] |
| Body Part Examined ◆ | Equals ◆ | CHEST | [+][-] |
| Study Description ◆ | Contains Any Of ◆ | CHEST THORAX | [+][-] |

[Save] [Cancel]

METHOD AND SYSTEM FOR RULE-BASED ANONYMIZED DISPLAY AND DATA EXPORT

RELATED APPLICATIONS

This application is a continuation in part of (1) U.S. application Ser. No. 14/611,163 filed Jan. 30, 2015 which is a continuation of (2) U.S. application Ser. No. 13/831,975 filed Mar. 13, 2013. This application also claims priority to (3) U.S. Provisional application No. 62/199,630 filed Jul. 31, 2015, the specification and drawings of (1)-(3) are herein expressly incorporated by reference in their entireties.

FIELD OF INVENTION

The invention pertains to rule based ways of anonymizing reports including medical diagnosis reports containing protected health information.

BACKGROUND OF THE INVENTION

In order to diagnose a traditional X-Ray examination, the images printed on films would be 'hung' in front of a light box. For multi-image examinations, as well as for comparison with priors, the 'hanging' would often follow a specific protocol. For example, a particular organization or doctor may choose for a two-view chest X-Ray with a two-view prior exam, that the films be hung from left to right as follows: Frontal view of current examination, lateral view of current examination, frontal view of prior examination, lateral view of prior examination. In contrast, the doctor may hang mammography exams with the corresponding views of current and prior next to each other, if that was more appropriate for the diagnostic workflow in that case. Thus, the organization or doctor developed a traditional 'Hanging Protocol'. Currently, the film and the light box are often being replaced by computer systems, called Picture Archiving and Communication System (PACS). PACS systems can mimic the Hanging Protocols.

Traditional X-Ray examinations typically produce one or a small number of single two dimensional (2D) images. In contrast, the more advanced imaging modalities such as Computer Tomography (CT), Magnetic Resonance Imaging (MRI) or Positron Emission Tomography (PET) can produce dozens of series, each consisting of a hundred or more images. It is possible and not uncommon to review images from these advanced modalities in the same manner as traditional X-Ray images, i.e., by hanging the individual images side-by-side, either on a light-box or using a PACS system.

In modern medicine, medical diagnosis reports are often digitized and contain information relating to the patient. Medical diagnosis reports include reports from clinical software systems such as in the field of radiology, where images are increasingly acquired and processed digitally. PACS, Radiology Information Systems (RIS) and similar computer systems are used to process and store the image data, as well as the patient information related to the images. The related information includes patient demographics, location and time of acquisition and other acquisition parameters. This non-pixel information is referred to as meta-data.

The meta-data is important for data management, e.g. for searching or identifying a particular data set relating to a particular exam, and it provides important information about the examination, which is relevant for the diagnostic interpretation of the images. Part of the meta-data (the Patient Identifiable Information (PII) and the Protected Health Information (PHI)) relate to the particular patient and allows identification of the patient.

SUMMARY OF THE INVENTION

The invention pertains to digital data processing and, more particularly, by way of example, to the visualization of image data. Three dimensional (3D) and four dimensional (4D) image data is routinely acquired with CT, MRI, PET, confocal microscopes, 3D ultrasound devices, and other imaging devices. The medical imaging market is just one example of a market that uses these devices. The visualization of image data market is growing rapidly, with new CT scanners collecting larger amounts of data more quickly than previous generation CT scanners. The invention has application to areas including medical imaging, atmospheric studies, astrophysics and geophysics.

With the rapid increase in the amounts and types of information that can be acquired using imaging technology, a substantial problem involves access to confidential information. Another substantial problem in the art, namely the increased likelihood of confusion of image-based information from different patients. In such situations, a physician or diagnostician may be presented with image-based information from different patients. Such inadvertent conflation can produce mis-diagnosis or mistaken non-diagnosis. In each case, the outcome for the patient can be serious, and can result in increased morbidity and mortality.

In an embodiment of the present invention, a rule based method for anonymizing PHI present in medical diagnostic reports is outlined. In an embodiment of the present invention, users with the appropriate permission based on their user ID can impose a function inside a system in order to anonymize the export of available studies, or one or more studies identified by a rule based criteria. The data from the studies that were identified is then anonymized on the system. In an embodiment of the present invention, the data from selected studies is anonymized on a server, and only then transmitted to another network device or stored to a hard disk or other media.

These and other aspects of the invention are evident in the drawings and in the description that follows.

BRIEF DESCRIPTION OF THE DRAWINGS

This invention is described with respect to specific embodiments thereof. Additional features can be appreciated from the Figures in which:

FIG. 3A shows an artist's impression of a dialog for exporting an exam with a De-Identification option, according to an embodiment of the invention;

FIG. 3B shows an artist's impression of the dialog to configure the De-Identification details, according to an embodiment of the invention;

FIG. 7 shows an example of a user interface to specify rules including a dialog box to configure Study Selection rules, according to an embodiment of the invention.

DETAILED DESCRIPTION OF THE INVENTION

Definitions

Figure 1:
FIG. 1 shows an artist's impression of a medical report with pseudo-Patient Identifiable Information (pseudo-PII), according to an embodiment of the invention.

The transitional term 'comprising' is synonymous with 'including', 'containing', or 'characterized by', is inclusive or open-ended and does not exclude additional, unrecited elements or method steps.

The transitional phrase 'consisting of' excludes any element, step, or ingredient not specified in the claim, but does not exclude additional components or steps that are unrelated to the invention such as impurities ordinarily associated with a composition.

The transitional phrase 'consisting essentially of' limits the scope of a claim to the specified materials or steps and those that do not materially affect the basic and novel characteristic(s) of the claimed invention.

The term 'client-server' refers to a computer system that selectively shares its resources; a client is a computer or computer program that initiates contact with a server in order to make use of a resource. This sharing of computer resources allows multiple people to use a computer server at the same time. Because a computer does a limited amount of work at any moment, a time-sharing system must quickly prioritize its tasks to accommodate the clients. Clients and servers exchange messages in a request-response messaging pattern: The client sends a request, and the server returns a response.

The phrase 'metadata entry' means data associated with a specific parameter in a medical diagnosis report. Metadata comprises both structural metadata and descriptive metadata. Structural metadata is information about the data. Descriptive metadata is the information content of the data.

The phrase 'phi of metadata' refers to PHI or PII in a medical diagnostic report. The phi of metadata is the information which makes up the descriptive metadata of a metadata entry related to PII or PHI.

The phrase 'institution aware ID' is a code that can be used to identify an institution for which the particular user ID is a member. An institution aware ID can be added to a phi of metadata to distinguish anonymized data from two separate institutions.

The phrase 'medical diagnosis' is the process of determining which disease or condition explains a person's symptoms and signs. The information required for diagnosis is typically collected from a medical history and physical examination of the person seeking medical care.

The phrase 'medical diagnostic report' means a report associated with a medical diagnosis where the medical diagnostic report contains data including PHI pertaining to the name, age and/or sex of the patient, medical history, physical examination and/or medical diagnosis of the patient, where at least some of the data is computer readable.

The term 'retrieving' means a process whereby a processor reads one or more phi of metadata from a medical diagnostic report.

The term 'accessing' means a process whereby a processor reads one or more phi of metadata from a medical diagnostic report and stores the one or more phi of metadata in one or more volatile computer memory locations.

The phrase 'server side cache' means cache associated with the server processor which is not directly accessible by a client processor.

The phrase 'combined value' means merging two or more phi of metadata, where each field of the one or more phi of metadata and their settings are copied into a new metadata field.

The term 'concatenating' means adding a separator character that is not part of the one or more phi of metadata to the one or more phi of metadata.

The phrase 'changing one or more phi of metadata' means adding computer readable data to one or more phi of metadata or deleting computer readable data from one or more phi of metadata, e.g., concatenating or combining.

The phrase 'separator character' means a designated computer readable character used to change one or more phi of metadata of the computer readable data by adding the separator character to the one or more phi of metadata, where the separator character is otherwise not used in the one or more phi of metadata.

The term 'computing' means using Central Processing Unit (CPU) or Graphics Processing Unit (GPU) to perform a calculation.

The phrase 'volatile computer memory location' means a memory location in a data structure which requires power to maintain the stored information such as volatile random access memory. The volatile computer memory location retains its contents only while the computer is connected to power. When the power is interrupted the stored data is immediately lost. When the volatile computer memory location is changed by adding or removing information, the memory location is overwritten. The word 'overwritten' means replacement of data in a data structure thereby removing the previous data and replacing it with the provided data.

The phrase 'secure value' means one or more phi of metadata corresponding to one or more PHI values for which the one or more phi of metadata have been changed such that the PHI cannot be ascertained.

The term 'anonymization' means to remove the possibility of ascertaining PHI values from a medical diagnostic report.

The phrase 'deidentified patient data' means a medical diagnostic report in which all PII and/or PHI values have been changed such that the PII and/or PHI cannot be ascertained.

The term 'Study' will be used to refer to the set of images produced by an examination. In an embodiment of the invention, a Study consists of one or more images. In an alternative embodiment of the invention, a Study consists of two or more images. The images can be grouped into one or more image series. Each image, each series, and the whole Study can have different parameters attached. For medical images these can be defined by the Digital Imaging and Communication in Medicine (DICOM) standard.

The phrase 'Hanging Protocol' will be used to refer to specific conventions how X-Ray films are arranged (hung) at a light box.

The phrase 'Display Protocol' will be used to refer to the way images are displayed in a computer system, specifically the selection of the images to be displayed, the layout of the images, as well as the rendering parameters and styles.

The term 'view' or 'viewing' means a display of a 3D or 2D image.

The term 'Viewport' will be used to refer to the logical part of the screen on the client computer in which a particular View is displayed, for example the user interface on the client computer can contain four rectangular Viewports 1160 of which three show a frontal, left, and bottom view respectively of a particular data, while the fourth viewer might show a 2D cross section through the same or a different data set.

The phrases 'Sets of Images' or 'Image Set' will be used to refer to one or more images, selected based on the rules.

The phrase 'Study Selection Rules' will be used to refer to the rules used to select and access the studies to be displayed including the anonymization of PHI and PII.

The phrase 'Protocol Selection Rules' will be used to refer to the rules used to select the layout of the images to be displayed.

The phrase 'Image Set Rules' will be used to refer to the rules used to form Image Sets 1165 from the images of one or more Study by applying selection, sorting, and breaking rules.

The phrase 'Style Rules' will be used to refer to the rules to determine which rendering type, rendering style, and rendering parameters are used for a particular Image Set 1165 in a particular viewer.

The phrase 'patient ID' refers to a code used to identify an individual patient.

The phrase 'user ID' refers to the access permissions associated with an individual user.

The phrase 'displaying a listing' or 'listing' means displaying a code or other abbreviated representation of a medical diagnostic report such that it can be selected, where displaying the listing does not display or otherwise access the information contained in the medical diagnostic report. Displaying the listing can be used to select the medical diagnostic report for viewing or other access.

The phrase 'displaying a medical diagnostic report' means displaying a medical diagnostic report such that the medical information but not necessarily the PHI and/or PII is displayed.

The phrase 'Protected Health Information', 'PHI', 'Patient Identifiable Information' or 'PII' are defined as the terms are used in the Health Insurance Portability and Accountability Act of 1996 (HIPAA) and other regulations relating to maintaining the privacy and security of individually identifiable health, financial or other information including Gramm-Leach-Bliley Act (GLBA), Federal Education Rights and Privacy Act (FERPA), Children's Online Privacy Protection Act (COPPA), Fair Credit Reporting Act (FCRA) the Health Information Technology for Economic and Clinical Health (HITECH) Act enacted as part of the American Recovery and Reinvestment Act of 2009 (ARRA), the Genetic Information Nondiscrimination (GINA) Act and other modifications of the HIPAA Rules. 'PHI' or 'PII' is any information that can be used on its own or with other information to identify, contact, locate or identify: a patient, a health status, a provision of health care or a payment for health care irrespective of how it is obtained and whether it is collected by or on behalf of an institution.

The phrase 'pseudo-Patient Identifiable Information' or 'pseudo-PII' means information that is used to simulate PII or PHI. Pseudo-PII does not and cannot function as PII or PHI. Pseudo-PII appears in the same format as PII or PHI, but because it is simulated it cannot be used on its own or with other information to identify, contact, locate or identify: a patient, a health status, a provision of health care or a payment for health care. Pseudo-PII rather than PII or PHI is displayed in this application in accordance with HIPAA, The Privacy Act, ARRA, COPPA, FERPA, FCRA, GLBA and HITECH to exemplify PII or PHI and the invention is applied to this pseudo-PII rather than to PII or PHI. Because the pseudo PII is in a similar format to the PII or PHI, the pseudo-PII can be used to exemplify the anonymization of PII or PHI using the invention.

The term 'display' means in the context of aspects and embodiments disclosed herein and refers in the usual and customary sense to physical representation of data e.g. a printed page or an electronic representation on a visual display monitor, a cathode ray oscilloscope, a liquid crystal display, a nixie tube, a light emitting diode display, a plasma display and the like.

The phrase 'Volume Rendering' will be used to refer to Volume Rendering techniques including shaded Volume Rendering techniques, maximum intensity projection (MIP), oblique slicing or multi-planar reformats (MPR), axial/sagittal and coronal slice display, and thick slices (also called slabs). In medical imaging, for example, Volume Rendering is used to display 3D images from 3D image data sets, where a typical 3D image data set is a large number of 2D slice images acquired by a CT or MRI scanner and stored in a data structure.

Overview

Often, the traditional 'Hanging Protocol' is either not intuitive, cannot display the information in a manner in which it can be reviewed or is not the most efficient way to display images. Alternative ways of rendering the acquired images can be more efficient or more appropriate for displaying the information. Examples include Volume Rendering techniques or maximum intensity projections of stacks of cross-sectional images, rendering of oblique slices, rendering of thick slices or slabs, or rendering of fused images (e.g. in PET/CT). Specialized diagnostic workstations that are often specific to a clinical application area are used to provide appropriate rendering of the acquired images. As organizations and doctors require better and faster visualization methods that allow users to interact with the image data in real-time, the requirements and demands for displaying the data will increase.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes. Furthermore, it will also be apparent that the present invention is not limited to any particular software programming language or programming paradigm.

While critical for the clinical workflow, there are a number of scenarios where no PII and/or PHI is required and the presence of the PII and/or PHI is even problematic. Due to health data and general privacy legislation, handling PII and/or PHI and passing on PII and/or PHI to other parties is often not possible, or comes with significant legal and contractual burden and potentially a business risk. The business risk is accentuated when the medical diagnosis report with the PII and/or PHI are shipped 'off shore' as the interpretation of what constitutes reasonable business practices can become subject to additional legal jurisdictions.

Examples for such scenarios include: scientific work, presentations in education, technical support and troubleshooting of problems in PACS, Imaging Worflow Solution, RIS, or similar computer systems, or generation of test data for software testing.

One approach to address the requirement for medical diagnosis reports without PII and/or PHI is to send images to a system for data anonymization, which creates a copy of the images, and strips the meta-data contained in the images or replaces them with default values. Such default value could be a patient ID of '00000', or an incrementing value such as ANON001, ANON002, . . . .

This approach has a number of problems, which the present rule based invention addresses. Firstly, the ability to automate anonymization and control permissions removes human error in controlling PII and/or PHI. Secondly, workflow of sending images to another system to anonymize, then export the data is cumbersome. Thirdly, anonymizing images individually, and individually deleting the patient identifiers or replacing them with default or random values, results in loss of any correlation information between multiple studies belonging to the same patient. In many cases, e.g. scientific use of the data, this is undesirable. This can be tackled by storing a table that maps real patient-identifiers to anonymized ones. This process is often referred to as 'pseudonymization'. Pseudonymization allows for re-identification of the anonymized data. However, for the same reasons that PII and/or PHI sharing can be undesirable, the ability to re-identify anonymized data through pseudonymization can be undesired. The present invention offers an alternative way to share medical diagnosis reports without the ability to re-identify PII and/or PHI. The display of sensitive information can be anonymized as described in U.S. patent application Ser. No. 15/218,993 titled 'Method and Apparatus for Anonymized Display and Data Export' filed Jul. 25, 2016 inventors D. Stalling et al., the specification and drawings of which are herein expressly incorporated by reference in their entirety.

Instead of mapping the patient ID to simple default values, the present invention uses a novel approach. A secure hash algorithm (SHA), such as SHA-1 is applied to the concatenation of a selected set of metadata fields. Typical sets of metadata fields are:
  Patient ID;
  Patient Name, Patient Birth Date, and patient gender; or
  Patient ID, Patient Name, Patient Birth Date, and patient gender.

The phrase 'secure hash function' means a hash function in which it is impossible to invert, that is, to recreate the input data from its hash value alone. Examples of secure hash function include MD4, MD5, SHA-1, SHA-2, Skein, and BLAKE.

The secure hash function has three main properties. Firstly, it is easy to compute the hash value for any given message. Secondly, it is not feasible to generate a message from its hash. Thirdly, it is not feasible to modify a message without changing the hash.

One secure hash function, Hashcash, uses partial hash inversions to prove that work was done, as a message which can be sent. Many secure hash functions, including MD4, MD5, SHA-1, SHA-2 and SHA-3 finalists Skein and BLAKE are built from block-cipher. Alternatively, the secure hash function Keccak, was built on a cryptographic sponge. Further, a standard block cipher such as AES can be used to build a secure hash function.

In an embodiment of the present invention, in order to compute the secure hash function on a given set of fields, the field values are concatenated, using a separator character that is not used in the phi or that is not part of the field values, such as for example a backslash '\'. In an embodiment of the present invention, let C be the concatenated value of the selected fields. Then M=SHA1(C) is the mapped ID, that is used in the anonymized data set, where SHA1 is the SHA-1 secure hash function, or another type of secure hash function. In an alternative embodiment of the present invention, an alternative secure hash function selected from the group consisting of MD4, MD5, SHA-2, Skein, BLAKE and AES is used.

FIG. 1 shows an artist's impression of a X-Ray image of a human thorax displayed in a PACS viewer. In FIG. 1, the darkness of the X-Ray image is indicated using a grey scale shading system where 905 is white, black is black and the values 910, 915, 920, 925, 930, 935 and 940 indicate shades of gray from lightest to darkest. The relevant information, including patient demographics is shown as text overlays. FIG. 1 depicts the display of a non-anonymized data set. Note in FIG. 1 the PII and/or PHI (including the names and dates) shown are pseudo-PII for the sake of illustrating the invention, and are not a real patient's PII and/or PHI. The Imaging Device Name corresponds with the device used to measure the displayed X-Ray image, however the invention can be used for other manufacturer's X-Ray image devices, for other PACS devices, for other diagnostic reports, for other medical reports and for other non-medical reports.

In the artist's impression of the medical report, pseudo-PII rather than PHI or PII is shown on the top left, top right and lower left (see FIG. 1). On the top left of FIG. 1 the 'Patient Name' is shown as SMITH MARY F, the 'Patient ID' as 12345 1932-May-09.76Y, the 'Exam ID' as EXM5678, the 'Study (Exam) Description' as THORAX AP, and the 'Study Date' as 2008-Oct-26. FIG. 1 also shows on the top right the 'Hospital Name' as SPRINGFIELD GENERAL HOSPITAL, the 'Imaging Device Name' KODAK Elite CR, and the 'Physician's Name' as Dr PETER JACKSON. Further, FIG. 1 shows on the lower left the 'Imaging Orientation' as AP, the 'Acquisition Time' as 16:42:42, and the 'Series/Image number' as 1 IMA 2.

Figure 2:
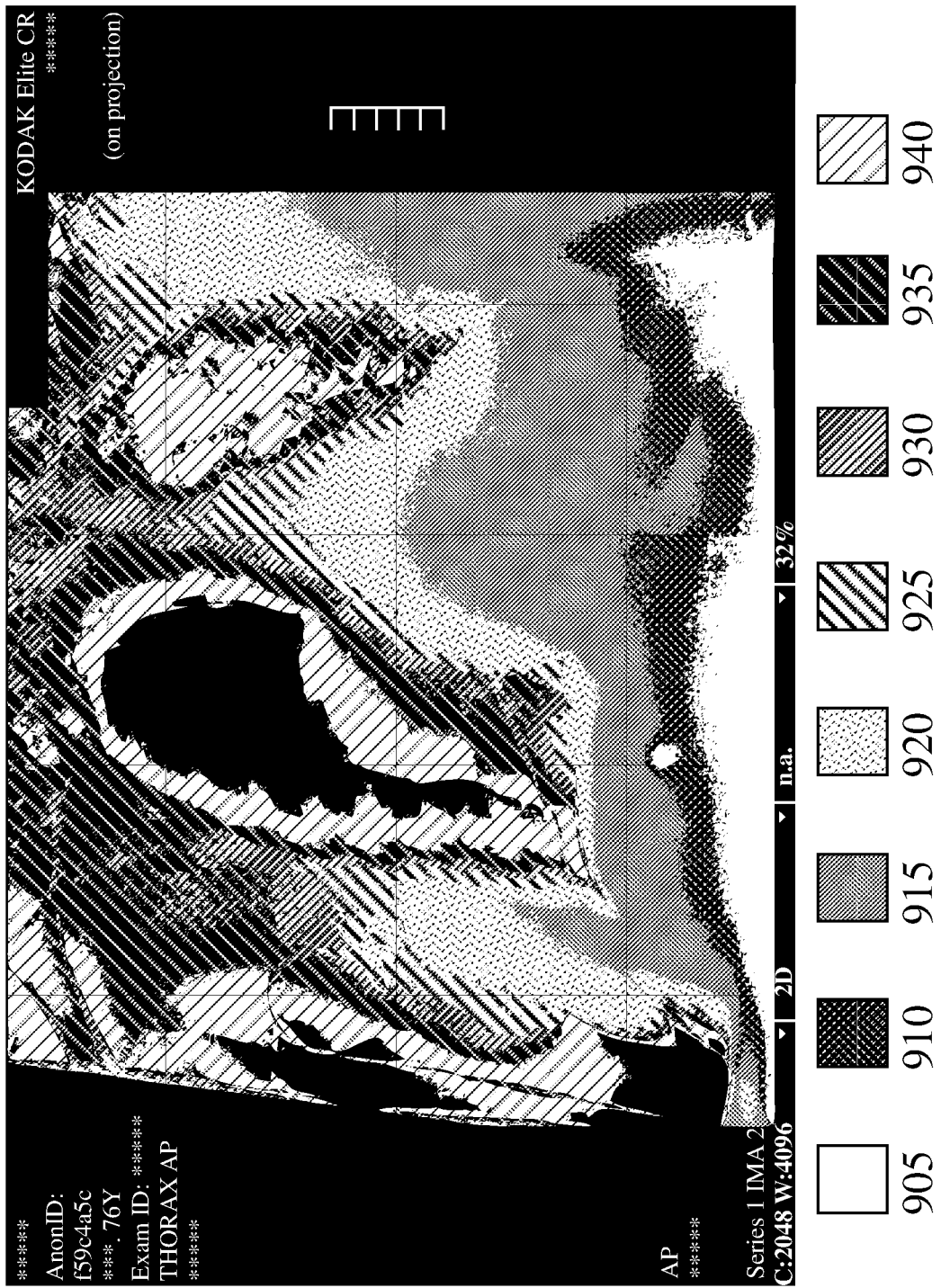
FIG. 2 shows an artist's impression of the medical report shown in FIG. 1 after anonymization in teaching mode, according to an embodiment of the invention.

FIG. 2 shows an artist's impression of the same study displayed when in the 'teaching mode'. In FIG. 2, the darkness of the image is indicated using a grey scale shading system where 905 is white, black is black and the values 910, 915, 920, 925, 930, 935 and 940 indicate shades of gray from lightest to darkest. In various embodiments of the invention, specific information is not displayed and replaced by "***" in the anonymized medical report when viewed in the teaching mode. On the top left in FIG. 2 the 'Patient Name' is *, the 'Patient ID' is replaced with 'AnonID' which is f59c4a5c*.76Y, the 'Exam ID' is *, the 'Study (Exam) Description' remains THORAX AP, and the 'Study Date' is *. On the top right, FIG. 2 does not show the 'Hospital Name', but still shows the 'Imaging Device Name' as KODAK Elite CR, and the 'Physician's Name' is *. Further, FIG. 2 shows on the lower left the 'Imaging Orientation' as AP, the 'Acquisition Time' is ***, and the 'Series/Image number' as 1 IMA 2. The Patient Birth Day is removed, but the patient's age (in years) is shown as 76Y.

In various embodiments of the invention the fields are configurable by a user. In alternative embodiments of the invention the fields are configurable by a user based on their userID. The Patient ID (PAT12345) is not shown, and instead the mapped id (computed as described herein) is shown with a prefix of AnonID. Thus, as shown in FIG. 2, the PII and/or PHI associated with the medical diagnostic report shown in FIG. 1 can be removed according to an embodiment of the present invention.

Figure 4:
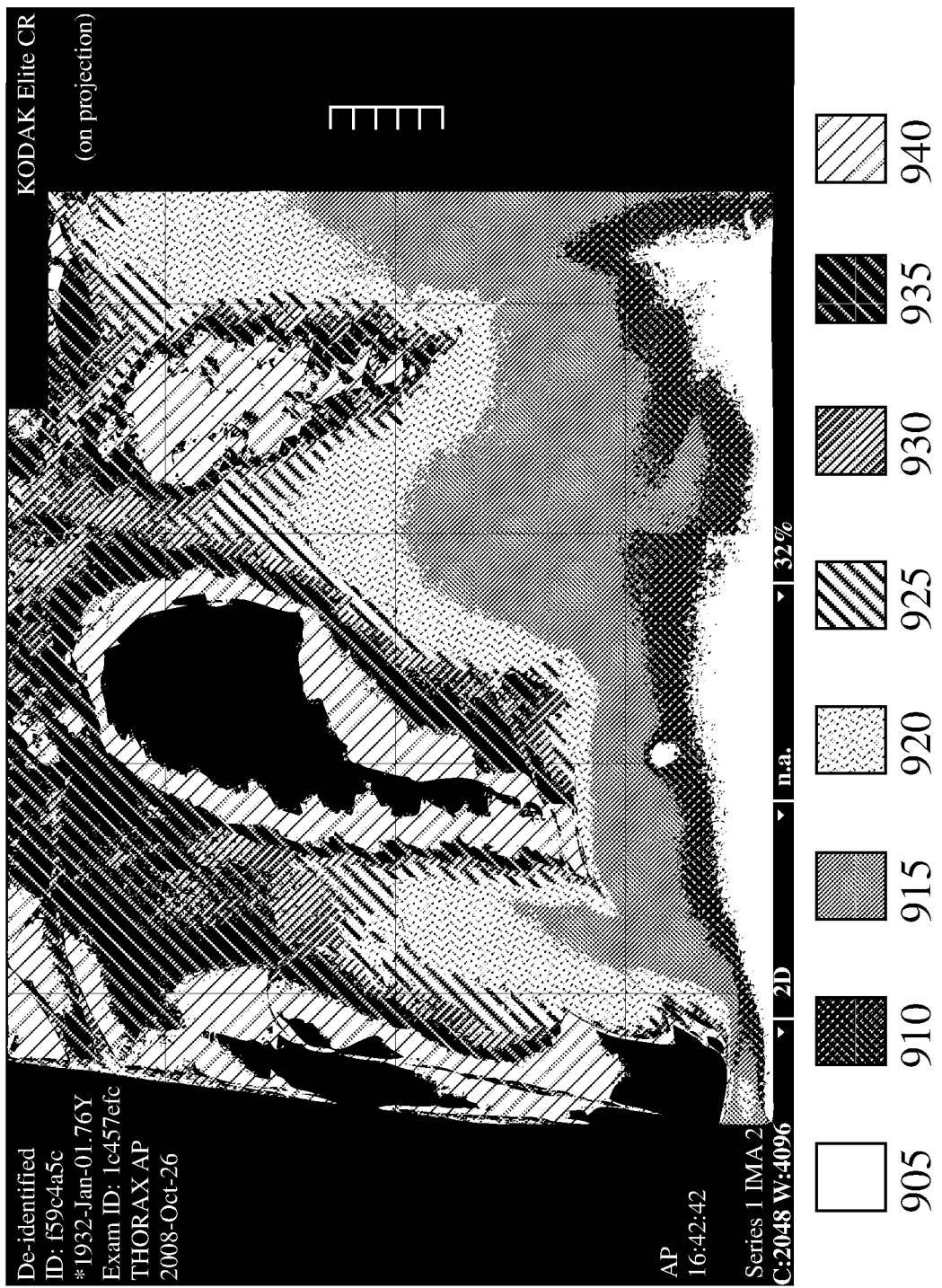
FIG. 4 shows an artist's impression of the medical report shown in FIG. 1 after export using the anonymization settings shown in FIG. 3B, according to an embodiment of the invention.

FIG. 3A shows an artist's impression of a dialog for exporting an exam. The dialog offers a De-Identification option. Clicking the Details button allows to configure the De-Identification. FIG. 3B shows an artist's impression of the dialog to configure the De-Identification details. Default values are filled in, depending on the system configuration. Note that in various embodiments of the invention, the fields that are affected by the anonymization may vary from system to system based on the exact use-case, the jurisdiction, changes in the Health Insurance Portability and Accountability Act (HIPAA), changes in other laws effecting the HIPAA regulations or other parameters. Accordingly, in various embodiments of the invention, the list can be configurable. In an embodiment of the invention, the ability to configure the list such as the configuration shown in FIG. 3B is password protected. In an embodiment of the invention, the ability to configure the list such as the configuration shown in FIG. 3B is password protected based on a security clearance. In various embodiments of the invention, a user with insufficient security clearance based on their user ID does not view the list as configurable. Note that in the configuration underlying FIG. 3B, the Study-Date and Study-Time Field are not affected by anonymization, while in the teaching mode configuration for FIG. 2 the Study-Date and Study-Time Field are anonymized. In various embodiments of the invention, these values can be overridden by a user with sufficient security clearance based on their user ID with either the original (un-anonymized values) or free-typed values. In the example configuration shown in FIG. 3B, the Patient ID field is pre-filled with the mapped patient ID as described herein. The accession number and study are pre-filled with unique random values. The Institution Name and Study Comment fields are left blank. FIG. 4 shows an artist's impression of a DICOM viewer displaying the images that were exported using the anonymization settings shown in FIG. 3B. In FIG. 4, the darkness of the DICOM viewer image is indicated using a grey scale shading system where 905 is white, black is black and the values 910, 915, 920, 925, 930, 935 and 940 indicate shades of gray from lightest to darkest. On the top left in FIG. 4 the 'Patient Name' is replaced with the label De-identified, the 'Patient ID' is replaced with 'ID' which is f59c4a5c*1932-Jan-01.76Y, the 'Exam ID' is 1c457efc, the 'Study (Exam) Description' remains THORAX AP, and the 'Study Date' is 2008-Oct-26. On the top right, FIG. 4 does not show the 'Hospital Name', but still shows the 'Imaging Device Name' as KODAK Elite CR, and the 'Physician's Name' is omitted. Further, FIG. 4 shows on the lower left the 'Imaging Orientation' as AP, the 'Acquisition Time' is 16:42:42, and the 'Series/Image number' as 1 IMA 2. Note that in an embodiment of the invention, in a 'teaching mode' only the viewer displays the data with anonymized PII and/or PHI. In an alternative embodiment of the invention, the information in the files is permanently anonymized and the viewer does not have to be in the 'teaching mode' to insure that the PII and/or PHI is not disclosed.

This approach has three very important characteristics. (i) It generates the same mapped id, if the input is the same. This means that two images belonging to the same patient can be exported independently, and without storing the mapped ID, both images will have the same mapped ID. (ii) Secure Hash Algorithms are not reversible. This means that even if the algorithm and the fields that are used to build the mapped ID are known, the value of the fields cannot be derived from the mapped ID. Therefore no re-identification is possible. (iii) The first characteristic (see (i) above) is achieved without storing the mapped value.

In multi-institution scenarios, where each institution independently assigns identifiers, the identifier that is used for one patient in one organization might also be used for a different patient in another organization. If data from both organizations are pooled, e.g. for a scientific study, this might lead to wrong conclusions, as images from different patients might seemingly relate to the same patient in the anonymized data set, as their patient ID and hence their mapped patient id would be the same. For example a first hospital might use Patient ID 1234 for one patient, while a second hospital might use the same ID 1234 for a different patient.

The present invention overcomes this issue by computing an institution aware mapped id. In an embodiment of the present invention, the institution name, or another institution identifier is added to the list of input fields to the secure hash function. Examples of suitable identifiers are DICOM tags (0008,0080) or (0010,0021). In this way, the mapped ID will be different for two patients with the same ID coming from two different hospitals. Note, that the secure hash function is not reversible. This means that it is not possible to determine the original patient ID from the mapped ID, nor is it possible to even determine the originating institution or hospital from the mapped ID.

SHA-1 and similar secure hash function are designed for cryptographic use. Most use cases described above do not require the same cryptographic strength, as the aim is not some kind of encryption. In an embodiment of the present invention, a subset of the phi of the SHA-1 function instead of the full set of phi of the SHA-1 function can be used in order to make identifiers not overly long.

In an embodiment of the present invention, in order to simplify the workflow the present invention integrates the anonymization into the data processing system (e.g. RIS, Imaging Workflow Solution, or PACS). In an embodiment of the present invention, a user based on their user ID with the associated permissions launches a function inside the system in order to anonymize and export the currently loaded study or studies, or one or more studies identified by search criteria. The data from the studies that were identified is then anonymized on the system. In an embodiment of the present invention, the data from the studies that were identified is then anonymized on the server, and only then transmitted to another network device or stored to a hard disk or other media.

This has key advantages compared to first exporting and then anonymizing. Besides increased efficiency, it ensures that the PII and/or PHI never leaves the original system, which is particularly important in situations where the medical diagnosis report is to be used off-shore.

Another scenario is the demonstration of clinical cases inside the organization, i.e. without any data export, but where not everybody in the audience might be entitled to see the PII and/or PHI, e.g. a lecture for students. Instead of creating anonymized copies in this case, the present invention allows on-the-fly anonymization. This saves significant amounts of time in educational institutions, such as university hospitals.

In an embodiment of the present invention, a user based on their user ID can start the client application of the clinical software system in a dedicated presentation mode. In an alternative embodiment of the present invention, a user based on their user ID can turn on a presentation mode so that from that point onwards information displayed on the screen that contains PII and/or PHI is replaced with the mapped values. Often, presentations are prepared by adding relevant cases to a worklist. However, it is also possible to open a case by typing in an original identifier, if the presenter has noted that in his or her preparatory notes. In an embodiment of the present invention, in the 'Anonymized Presentation Mode', any PII and/or PHI text fields used for searching will not display the actual characters typed in, but instead just show dots or other replacement characters. In this way the presenter can open relevant cases in front of the audience, e.g. using a video projector, without cumbersome preparatory work, and without disclosing PII and/or PHI. While a student viewing the presentation can make a notation of an output, that output has only value as confirming the output. That is, if after the presentation the student asks the presenter a question about that output, the notation cannot be used to retrieve the presentation. However, if the presenter retrieves the output (by typing in the appropriate input), the output when displayed will have the same notation, and thus confirm that this was the presentation to which the question related.

In an embodiment of the invention, a method for displaying medical diagnostic reports comprises the steps of receiving one or more medical diagnostic reports, retrieving one or more phi of metadata containing PHI in the one or more medical diagnostic reports, computing one or more concatenated values for the one or more phi of metadata using a separator character, computing one or more secure values for the one or more concatenated values using a secure hash function and displaying the one or more medical diagnostic reports, where the secure value is substituted for each phi of the one or more phi of metadata.

In an embodiment of the invention, a method for exporting medical diagnostic reports comprises the steps of receiving a medical diagnostic report, retrieving a phi of PHI and/or PHI (PII)j, for each j, where j is an integer between 1 and J, where J is the number of phi of PII and/or PHI, computing a concatenated value ($C_j$) for each $PII_j$, for each j, where j is an integer between 1 and J, computing a $M_j$, where $M_j$ is given by $SHA1(C_j)$, for each j, where SHA1 is the SHA-1 secure hash function and exporting the medical diagnostic report, where one or more $M_j$ are substituted for one or more $PII_j$, for each j.

In an embodiment of the invention, a method for displaying medical diagnostic reports comprises the steps of receiving one or more medical diagnostic reports, retrieving one or more phi of metadata in the one or more medical diagnostic reports, computing one or more concatenated values for the one or more phi of metadata using a separator character, computing one or more secure values for the one or more concatenated values using a secure hash function and exporting the one or more medical diagnostic reports, where the one or more secure values are substituted for the one or more phi metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing PHI in the one or more medical reports, computing a concatenated value for each of the one or more phi of metadata using a separator character, computing a secure value for each of the concatenated values using a secure hash function and exporting to the first client the one or more medical diagnostic reports, where the secure value is substituted for each phi of the one or more phi of metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing PHI in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES and exporting to the first client the one or more medical diagnostic reports, where the secure value is substituted for each phi of the one or more phi of metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing PHI in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES, where the secure hash function displayed cannot be reversed to generate the corresponding phi of metadata and exporting to the first client the one or more medical diagnostic reports, where the secure value is substituted for each phi of the one or more phi of metadata in the one or more exported medical diagnostic reports.

In an embodiment of the invention, a system for exporting medical diagnostic reports comprises a server digital data processor, the server digital data processor in communications coupling with one or more client digital data processors, the server digital data processor including an anonymization program, executing on the server digital data processor, the anonymization program responding to a request from a first client on a first client digital data processor of the one or more client digital data processors by executing one or more anonymization commands, comprising the steps of receiving one or more medical diagnostic reports designated by the first client, retrieving one or more phi of metadata containing PHI in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES, where the secure hash function displayed cannot be reversed to generate the corresponding phi of metadata, where the secure hash function displayed in a first medical report is the same as the secure hash function displayed in a second medical report when the corresponding phi of metadata in the first medical report is the same as the corresponding phi of metadata in the second medical report and exporting to the first client the one or more medical diagnostic reports, where the secure value is substituted for each phi of the one or more phi of metadata in the one or more exported medical diagnostic reports.

In an embodiment of the invention, a method for displaying medical diagnostic reports comprises the steps of receiving one or more medical reports, retrieving one or more phi of metadata containing PHI in the one or more medical reports, computing a concatenated value for each of the one or more phi of metadata using a separator character, computing a secure value for each of the concatenated values using a secure hash function and displaying the one or more medical reports, where the secure value is substituted for each phi of the one or more phi of metadata.

In an embodiment of the invention, a method for displaying medical diagnostic reports comprises the steps of receiving one or more medical reports, retrieving one or more phi of metadata containing PHI in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES and displaying the one or more medical reports, where the secure value is substituted for each phi of the one or more phi of metadata.

In an embodiment of the invention, a method for displaying medical diagnostic reports comprises the steps of receiving one or more medical reports, retrieving one or more phi of metadata containing PHI in the one or more medical reports, computing a concatenated value for each of the one or more phi of metadata using a separator character, computing a secure value for each of the concatenated values using a secure hash function and exporting the one or more medical reports, where the secure value is substituted for each phi of the one or more phi of metadata in the one or more exported medical reports.

In an embodiment of the invention, a method for displaying medical diagnostic reports comprises the steps of receiving one or more medical reports, retrieving one or more phi of metadata containing PHI in the one or more medical reports, computing a concatenated value for each of the one or more phi of metadata using a separator character, computing a secure value for each of the concatenated values using a secure hash function selected from the group consisting of MD4, MD5, SHA-1, SHA-2, Skein, BLAKE and AES and exporting the one or more medical reports, where the secure value is substituted for each phi of the one or more phi of metadata in the one or more exported medical reports.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and displaying the one or more medical reports, where the one or more secure values are substituted for the one or more phi of metadata.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function selected from the group consisting of MD4, MD5, SHA-1, SHA-2, Skein, and BLAKE and displaying the one or more medical reports, where the one or more secure values are substituted for the one or more phi of metadata.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and displaying the one or more medical reports, where the one or more secure values are substituted for the one or more phi of metadata, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a method for displaying medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and displaying the one or more medical reports, where the one or more secure values are substituted for the one or more phi of metadata, where a first secure value displayed corresponding to a first phi of metadata in a first medical report is the same as a second secure value corresponding to a second phi of metadata displayed in a second medical report when the first phi of metadata is the same as the second phi of metadata, where when the first secure value displayed is the same as the second secure value does not rely on storing one or both the first secure value and the second secure value.

In an embodiment of the invention, a method that displays an anonymized medical report comprising the steps of receiving a medical report, retrieving one or more phi of PHI and/or PII (PIIj), where j is an integer between 1 and J, where J is the number of phi of PII and/or PHI in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J.

In an embodiment of the invention, a method that displays an anonymized medical report comprising the steps of receiving a medical report, retrieving one or more phi of PII and/or PHI (PIIj), where j is an integer between 1 and J, where J is the number of phi of PII and/or PHI in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, where in the displayed medical report the one or more Mj cannot be used to generate the one or more PIIj.

In an embodiment of the invention, a method that displays an anonymized medical report comprising the steps of receiving a medical report, retrieving one or more phi of PHI and/or PII (PIIj), where j is an integer between 1 and J, where J is the number of phi of PII and/or PHI in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, where a first Mj (j=1) displayed in a first medical report is the same as a second Mj (j=2) displayed in a second medical report when $PII_1$ in the first medical report is equal to $PII_2$ in the second medical report.

In an embodiment of the invention, a method that displays an anonymized medical report comprising the steps of receiving a medical report, retrieving one or more phi of PHI and/or PII (PIIj), where j is an integer between 1 and J, where J is the number of phi of PII and/or PHI in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, where a first Mj (j=1) displayed in a first medical report is the same as a second Mj (j=2) displayed in a second medical report when $PII_1$ in the first medical report is equal to $PII_2$ in the second medical report, where when displaying two medical reports $M_1$ in a first medical report is equal to $M_2$ in a second medical report does not rely on storing one or both $M_1$ and $M_2$.

In an embodiment of the invention, a method that displays an anonymized medical report comprising the steps of receiving a medical report, retrieving one or more phi of PHI and/or PII (PIIj), where j is an integer between 1 and J, where J is the number of phi of PII and/or PHI in the medical report, computing one or more concatenated values (Cj) for each PIIj, where j is an integer between 1 and J, computing one or more Mj, where Mj is given by SHA1(Cj), where j is an integer between 1 and J, where SHA1 is SHA-1 secure hash function and displaying the medical report, where one or more Mj are substituted for one or more PIIj, where j is an integer between 1 and J, further comprising using a separator character between each Mj, where the separator character is not a value present in the one or more PIIj, where j is an integer between 1 and J.

In an embodiment of the invention, a method for exporting medical reports comprising the steps of receiving one or more medical reports, retrieving one or more phi of metadata in the one or more medical reports, computing one or more concatenated values for the one or more phi of metadata using a separator character, computing one or more secure values for the one or more concatenated values using a secure hash function and exporting the one or more medical reports, where the one or more secure values are substituted for the one or more phi of metadata.

In an embodiment of the invention, a method for anonymization of medical reports comprising the steps of receiving one or more medical reports, retrieving one or more phi of metadata in the one or more medical reports, computing one or more concatenated values for the one or more phi of metadata, computing one or more secure values for the one or more concatenated values using a secure hash function and substituting the one or more secure values for the one or more phi of metadata in the medical reports.

In an embodiment of the invention, a method for anonymization of medical reports comprising the steps of receiving one or more medical reports, retrieving one or more phi of metadata containing PHI in the one or more medical reports, computing one or more secure values for the one or more phi of metadata using a secure hash function and substituting the one or more secure values for the one or more phi of metadata.

In an embodiment of the invention, a method for anonymization of medical reports comprising the steps of receiving one or more medical reports, retrieving one or more phi of metadata containing PHI in the one or more medical reports, adding an institution aware ID to the one or more phi of metadata, computing one or more concatenated values for the one or more phi of metadata, computing one or more secure values for the one or more concatenated values using a secure hash function and anonymizing the one or more medical reports, where the one or more secure hash functions are substituted for the one or more phi of metadata.

In an embodiment of the invention, a method for anonymization of medical reports comprising the steps of receiving one or more medical reports, retrieving one or more phi of metadata containing PHI in the one or more medical reports, adding an institution aware ID to the one or more phi of metadata, computing one or more concatenated values for the one or more phi of metadata, computing one or more secure values for the one or more concatenated values using a secure hash function selected from the group consisting of MD4, MD5, SHA-1, SHA-2, Skein, BLAKE and AES and anonymizing the one or more medical reports, where the one or more secure hash functions are substituted for the one or more phi of metadata.

In an embodiment of the invention, a method for anonymization of medical reports comprising the steps of receiving one or more medical reports, retrieving one or more phi of metadata containing PHI in the one or more medical reports, generating one or more combined values by adding an institution aware ID to the one or more phi of metadata, computing one or more secure values for the one or more combined values using a secure hash function and anonymizing the one or more medical reports, where the one or more secure values are substituted for the one or more phi of metadata.

In an embodiment of the invention, a method for anonymization of medical reports comprising the steps of receiving one or more medical reports, retrieving one or more phi of metadata containing PHI in the one or more medical reports, generating one or more combined values by adding an institution aware ID to the one or more phi of metadata, computing one or more secure values for the one or more combined values using a secure hash function selected from the group consisting of MD4, MD5, SHA-1, SHA-2, Skein, BLAKE and AES and anonymizing the one or more medical reports, where the one or more secure values are substituted for the one or more phi of metadata.

In an embodiment of the invention, a method for anonymization of medical reports comprising the steps of receiving one or more medical reports, retrieving one or more phi of metadata containing PHI in the one or more medical reports, generating one or more combined values by adding an institution aware ID to the one or more phi of metadata, concatenating the one or more phi of metadata prior to adding an institution aware ID, computing one or more secure values for the one or more combined values using a secure hash function and anonymizing the one or more medical reports, where the one or more secure values are substituted for the one or more phi of metadata.

In an embodiment of the invention, a method that displays an anonymized medical report comprising the steps of receiving a medical report, retrieving one or more phi of PHI and/or PII (PII)j, where j is an integer between 1 and J, where J is the number of phi of PII and/or PHI, computing a concatenated value (Cj) for each PIIj, where j is an integer between 1 and J, computing one or more Mj, where Mj is given by SF(Cj), where j is an integer between 1 and J, where SF is a secure hash function and displaying the medical report, where one or more Mj is substituted for each PIIj.

In an embodiment of the invention, a method that displays an anonymized medical report comprising the steps of receiving a medical report, retrieving one or more phi of PHI and/or PII (PII)j, where j is an integer between 1 and J, where J is the number of phi of PII and/or PHI, computing a concatenated value (Cj) for each PIIj, where j is an integer between 1 and J, computing one or more Mj, where Mj is given by SF(Cj), where j is an integer between 1 and J, where SF is a secure hash function selected from the group consisting of MD4, MD5, SHA-1, SHA-2, Skein, BLAKE and AES and displaying the medical report, where one or more Mj is substituted for each PIIj.

In an embodiment of the invention, a method comprises accessing one or more medical diagnostic reports, retrieving one or more phi of metadata containing PHI in the one or more medical diagnostic reports, storing the one or more phi of metadata, adding an institution aware ID to the one or more phi of metadata to generate one or more combined values, concatenating the one or more combined values with a separator character to generate one or more concatenated values, computing one or more secure values from the one or more concatenated values, overwriting the one or more phi of metadata with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing PHI in the one or more medical diagnostic reports, storing the one or more phi of metadata, adding an institution aware ID to the one or more phi of metadata to generate one or more combined values, concatenating the one or more combined values with a separator character to generate one or more concatenated values, computing one or more secure values from the one or more concatenated values using a secure hash function, overwriting the one or more phi of metadata with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing PHI in the one or more medical diagnostic reports, storing the one or more phi of metadata, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, overwriting the one or more phi of metadata with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing PHI in the one or more medical diagnostic reports, storing the one or more phi of metadata in a volatile computer memory location, adding an institution aware ID to the one or more phi of metadata to generate one or more combined values, concatenating the one or more combined values with a separator character to generate one or more concatenated values, computing one or more secure values from the one or more concatenated values, overwriting the one or more phi of metadata in the volatile computer memory location with the one or more secure values and displaying on a visual monitor the one or more medical diagnostic reports, where the one or more secure values are substituted for the one or more phi of metadata, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a method comprises accessing one or more medical diagnostic reports, retrieving one or more phi of metadata containing PHI in the one or more medical diagnostic reports, storing the one or more phi of metadata in a volatile computer memory location, adding an institution aware ID to the one or more phi of metadata to generate one or more combined values, concatenating the one or more combined values with a separator character to generate one or more concatenated values, computing one or more secure values from the one or more concatenated values, overwriting the one or more phi of metadata in the volatile computer memory location with the one or more secure values and displaying on a visual monitor the one or more medical diagnostic reports, where the one or more secure values are substituted for the one or more phi of metadata.

In an embodiment of the invention, a method comprises accessing one or more medical diagnostic reports, retrieving one or more phi of metadata containing PHI in the one or more medical diagnostic reports, storing the one or more phi of metadata, adding an institution aware ID to the one or more phi of metadata to generate one or more combined values, concatenating the one or more combined values with a backslash character to generate one or more concatenated values, computing one or more secure values from the one or more concatenated values, overwriting the one or more phi of metadata with the one or more secure values and displaying on a visual monitor the one or more medical diagnostic reports, where the one or more secure values are substituted for the one or more phi of metadata In an embodiment of the invention, a method comprises accessing one or more medical diagnostic reports, retrieving one or more phi of metadata containing PHI in the one or more medical diagnostic reports, storing the one or more phi of metadata, adding an institution aware ID to the one or more phi of metadata to generate one or more combined values, where the institution aware ID is a DICOM tag (00zz,00xx) where zz and xx are integers between 1 and 99 selected to unambiguously identify the institution from one or more other institutions, concatenating the one or more combined values with a separator character to generate one or more concatenated values, computing one or more secure values from the one or more concatenated values, overwriting the one or more phi of metadata with the one or more secure values and displaying on a visual monitor the one or more medical diagnostic reports, where the one or more secure values are substituted for the one or more phi of metadata.

In an alternative embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function, generating one or more first amended medical diagnostic reports, where in the one or more medical diagnostic reports one or more of the one or more phi of metadata are overwritten with one or more secure values and exporting to the first client digital data processor the one or more first amended medical diagnostic reports.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, generating one or more first amended medical diagnostic reports, where in the one or more medical diagnostic reports one or more of the one or more phi of metadata are overwritten with one or more secure values and exporting to the first client digital data processor the one or more first amended medical diagnostic reports.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where one or both the one or more phi of metadata and the one or more secure values are stored in a volatile memory location.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a backslash character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where the institution aware ID is a DICOM tag (00zz,00xx) where zz and xx are integers between 1 and 99 selected to unambiguously identify an institution from one or more institutions.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where the one or more secure values cannot be used to generate the one or more phi of metadata.

In an embodiment of the invention, a system comprises at least a first client digital data processor, an anonymization program and a server digital data processor, the server digital data processor in communications coupling with the first client digital data processor, the server digital data processor responding to a request from the first client digital data processor to export one or more medical diagnostic reports by executing the anonymization program which directs the server digital data processor to execute one or more commands including retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values and exporting to the first client digital data processor the one or more first amended medical diagnostic reports, where the system is adapted to receive instructions from the first client digital data processor to generate one or more second amended medical diagnostic reports, where in the one or more medical diagnostic reports all of the one or more phi of metadata are overwritten with one or more secure values and export to a second client digital data processor the one or more second amended medical diagnostic reports.

In another embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing PHI in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more amended medical diagnostic reports, where the one or more phi of metadata in the one or more medical diagnostic reports are overwritten with one or more secure values and displaying the one or more amended medical diagnostic reports.

In an embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing PHI in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function, generating one or more amended medical diagnostic reports, where the one or more phi of metadata in the one or more medical diagnostic reports are overwritten with one or more secure values and displaying the one or more amended medical diagnostic reports.

In an embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing PHI in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, generating one or more amended medical diagnostic reports, where the one or more phi of metadata in the one or more medical diagnostic reports are overwritten with one or more secure values and displaying the one or more amended medical diagnostic reports In an embodiment of the invention, a device comprises a computer readable physical medium having computer-executable instruction contained therein for execution on a processor, where when the computer-executable instructions are executed by the processor a method is carried out comprising the following steps, retrieving one or more phi of metadata containing PHI in one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more amended medical diagnostic reports, where the one or more phi of metadata in the one or more medical diagnostic reports are overwritten with one or more secure values and displaying the one or more amended medical diagnostic report, where a first secure value displayed in the one or more amended medical diagnostic reports corresponding to a first phi of metadata in a first medical report is the same as a second secure value corresponding to a second phi of metadata displayed in a second medical report when the first phi of metadata is the same as the second phi of metadata.

In an embodiment of the invention, a non-transitory computer readable physical storage medium comprising a set of computer-readable instructions stored thereon which, when executed by a processing system, cause the processing system to retrieve one or more phi of metadata containing PHI in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values, generate one or more amended medical diagnostic reports, where the one or more phi of metadata in the one or more medical diagnostic reports are overwritten with one or more secure values and display the one or more amended medical diagnostic reports.

In an embodiment of the invention, a non-transitory computer readable physical storage medium comprising a set of computer-readable instructions stored thereon which, when executed by a processing system, cause the processing system to retrieve one or more phi of metadata containing PHI in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values using a secure hash function, generate one or more amended medical diagnostic reports, where the one or more phi of metadata in the one or more medical diagnostic reports are overwritten with one or more secure values and display the one or more amended medical diagnostic reports.

In an embodiment of the invention, a non-transitory computer readable physical storage medium comprising a set of computer-readable instructions stored thereon which, when executed by a processing system, cause the processing system to retrieve one or more phi of metadata containing PHI in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values using a secure hash function selected from the group consisting of MD4, MD5, SHA-1, SHA-2, Skein, and BLAKE, generate one or more amended medical diagnostic reports, where the one or more phi of metadata in the one or more medical diagnostic reports are overwritten with one or more secure values and display the one or more amended medical diagnostic reports.

In an embodiment of the invention, a non-transitory computer readable physical storage medium comprising a set of computer-readable instructions stored thereon which, when executed by a processing system, cause the processing system to retrieve one or more phi of metadata containing PHI in one or more medical diagnostic reports, in which the set of instructions, when executed by the processing system, further cause the processing system to perform the steps of add an institution aware ID to the one or more phi of metadata to generate one or more combined values, concatenate the one or more combined values with a separator character to generate one or more concatenated values, compute one or more secure values from the one or more concatenated values, generate one or more amended medical diagnostic reports, where the one or more phi of metadata in the one or more medical diagnostic reports are overwritten with one or more secure values and display the one or more amended medical diagnostic reports, where a first secure value displayed in the one or more amended medical diagnostic reports corresponding to a first phi of metadata in a first medical report is the same as a second secure value corresponding to a second phi of metadata displayed in a second medical report when the first phi of metadata is the same as the second phi of metadata.

In a different embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function selected from the group consisting of MD4, MD5, SHA-1, SHA-2, Skein, and BLAKE, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values using a secure hash function, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic report, where one or both the one or more phi of metadata and the one or more secure values are stored in a volatile memory location.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a backslash character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports, where the institution aware ID is a DICOM tag (00zz,00xx) where zz and xx are integers between 1 and 99 selected to unambiguously identify an institution from one or more institutions.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports, where in the one or more medical diagnostic reports one or more of the one or more phi of metadata are overwritten with one or more secure values, where the one or more phi of metadata are overwritten with the one or more secure values and exporting to the first client digital data processor the one or more first amended medical diagnostic reports, where the one or more secure values cannot be used to generate the one or more phi of metadata.

In an embodiment of the invention, a method comprises retrieving one or more phi of metadata containing PHI in the one or more medical diagnostic reports, adding an institution aware ID to the one or more phi of metadata to generate one or more combined values, concatenating the one or more combined values with a separator character to generate one or more concatenated values, computing one or more secure values from the one or more concatenated values, generating one or more first amended medical diagnostic reports and one or more second amended medical diagnostic reports, where in the one or more medical diagnostic reports one or more of the one or more phi of metadata are overwritten with the one or more secure values to generate the one or more first amended medical diagnostic reports and all of the one or more phi of metadata are overwritten with the one or more secure values to generate the one or more second amended medical diagnostic report, where the one or more phi of metadata are overwritten with the one or more secure values and exporting to the first client digital data processor the one or more first amended medical diagnostic reports and exporting to the second digital data processor the one or more second amended medical diagnostic reports.

In general aspects of this invention, a First Study is first selected for review by a physician or diagnostician. Selection of a Study will generally be based on some particular characteristic. Such characteristic can be anatomical, disease-based, or both. Once a First Study is selected, an Additional Candidate Study can be selected based on the anatomical location of the First Study. Therefore, if the First Study is a Chest X-Ray, an Additional Candidate Study can be a Chest CT scan, MRI, positron-emission tomography (PET) scan, or other image of the chest. Alternatively, if a First Study is an X-Ray image of the gastrointestinal tract, an Additional Candidate Study could be a series of X-Ray images taken after ingestion of a contrast agent (such as barium). It can be appreciated that such anatomically selected Additional Candidate Studies can be applied to any organ, organ system, or tissue.

Alternatively, Additional Candidate Studies can be selected based on the type of disorder of disease being evaluated. For example, in a case in which a patient has had a diagnosis of cancer of one organ (e.g., lung), it can be desirable for Additional Candidate Studies to be targeted to identification of metastases in another organ. Thus, if a First Study is a Chest X-Ray, an Additional Candidate Study can be of the lymphatic system, head and neck, or various abdominal quadrants. Such Additional Candidate Studies may be X-ray, CT scans, MRI scans, PET scans, vascular visualizations (e.g., with injected contrast media) or histological images taken during a biopsy. Because the degree of detail (i.e., "granularity") obtained using different imaging techniques may vary widely it can be desirable to have a Rule Based process whereby the granularity of an Additional Candidate Study is increased over that of the First Study.

For example, a Chest X-Ray is a two-dimensional image in which the entirety of the chest and lungs is represented as a flat image. An Additional Candidate Study could be a CT scan, where "2-dimensional" images are acquired at a series of different "depths" (e.g., "slices") through the organ. If the 2-dimensional images are of sufficient quality to produce a 3-dimensional image of the organ with desirable degree of granularity, then the Additional Candidate Study can be depicted and displayed along with the image of the First Study.

General Rule 1 for selecting an Additional Candidate Study therefore can be: IF (Primary.Dicom.BodyPartExamined) is "ANATOMICAL REGION 1", and (Primary.Dicom.Modality=IMAGE TYPE 1").

THEN SELECT other studies for loading, WHERE (Other.Dicom.BodyPart Examined=ANATOMICAL REGION 1") and (Other.Dicom.Modality="IMAGE TYPE 2").

If desired, in General Rule 1, Additional Candidate Studies can target "Other.Dicom.Modality="IMAGE TYPE 2").

It can be appreciated that any number of Additional Candidate Studies can be integrated using the computer-based processes of this invention.

Alternatively, General Rule 2 for selecting an Additional Candidate Study therefore can be:

IF (Primary.Dicom.Disease) is "DISEASE 1", and (Primary.Dicom.Modality=IMAGE TYPE 1")

THEN SELECT other studies for loading, WHERE (Other.Dicom.Disease)="DISEASE 1") and (Primary.Dicom.Modality="IMAGE TYPE 2").

It can be readily appreciated that application of General Rule 2 can integrate other Anatomical Regions and a number of different Image Types. It can also be appreciated that using "DICOM" in the rules, the likelihood of conflation of images from different patients can be substantially or completely eliminated.

Additionally, to consider information derived from different patients simultaneously, the selection for "DICOM" can be in a First Study, "DICOM 1" and THEN SELECT an image from "DICOM 2." Integrating this additional feature into a Rule Based computerized system can permit detection and analysis of disease "clusters" (e.g., cancer clusters; toxin-induced clusters, infection clusters, and the like).

In an embodiment of the present invention, a method or system uses a rule derived basis to display image sets. In various embodiments of the present invention, the selection of the images to be displayed, the layout of the images, i.e., the hanging, as well as the rendering parameters and styles can be determined using a rule derived basis. In an embodiment of the present invention, each user based on their user ID is presented with images displayed based on their preferences without having to first manually adjust parameters. Accordingly, there is a time saving in not displaying images initially in a non-rule derived basis.

Figure 6:
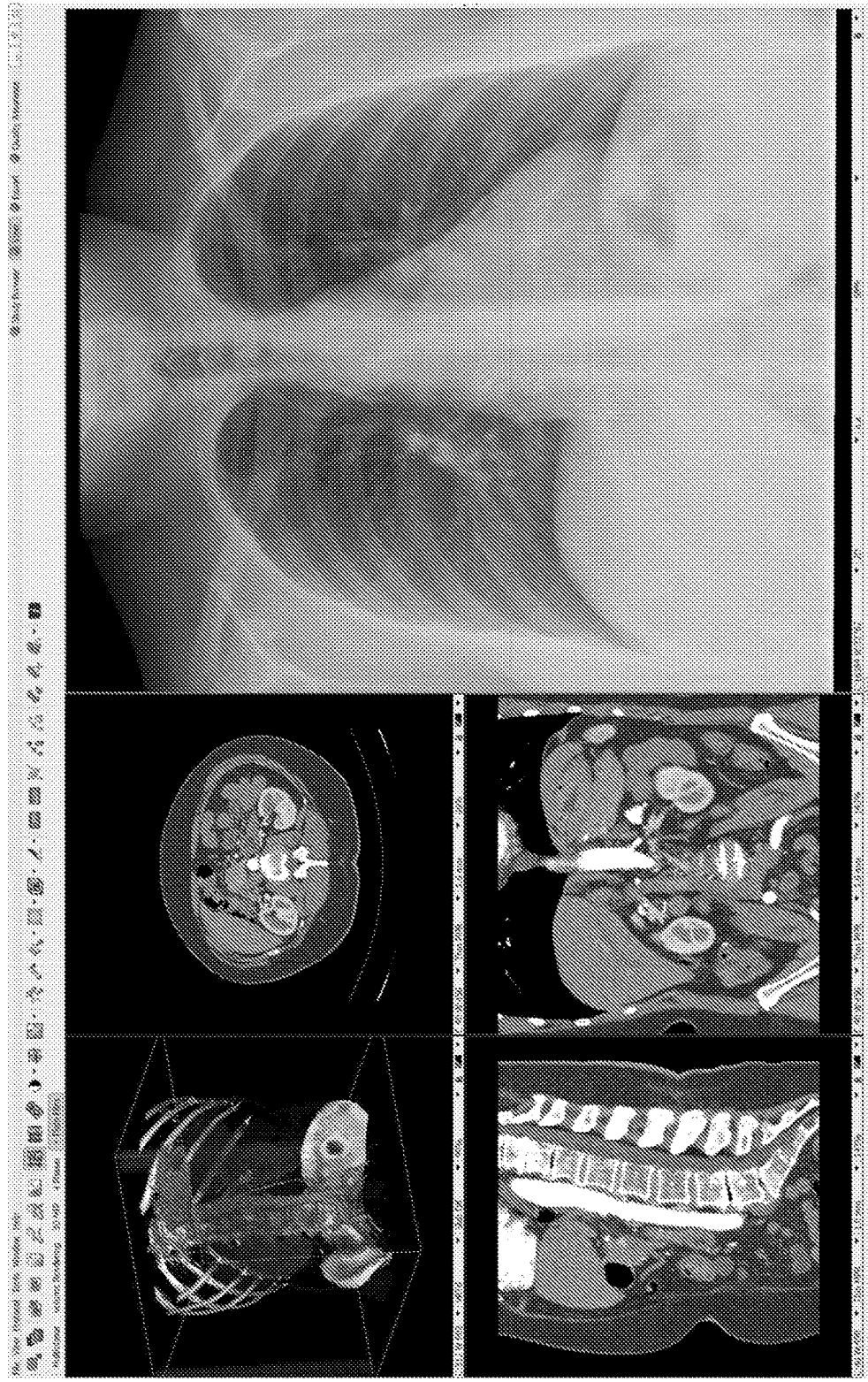
FIG. 6 depicts the resulting display for an example study, according to an embodiment of the invention.

FIG. 6 depicts an example study where the rules have created two Sets of Images. One Set of Images consists of a series of CT images forming a 3D volume, which is depicted in a volume rendered style in the Viewport 1160 in the upper left and in three orthogonal cross sections in the three other viewports in the left half of the screen. The second Set of Images consist of one chest X-Ray, assigned to a single Viewport 1160 covering the right half of the screen and rendering the X-Ray in 2D style. Appropriate data windows have been chosen by the rules to highlight the vasculature in the 3D rendering, as this is a study with contrast, as the rules can determine by the StudyDescription containing the word 'contrast'.

Figure 5:
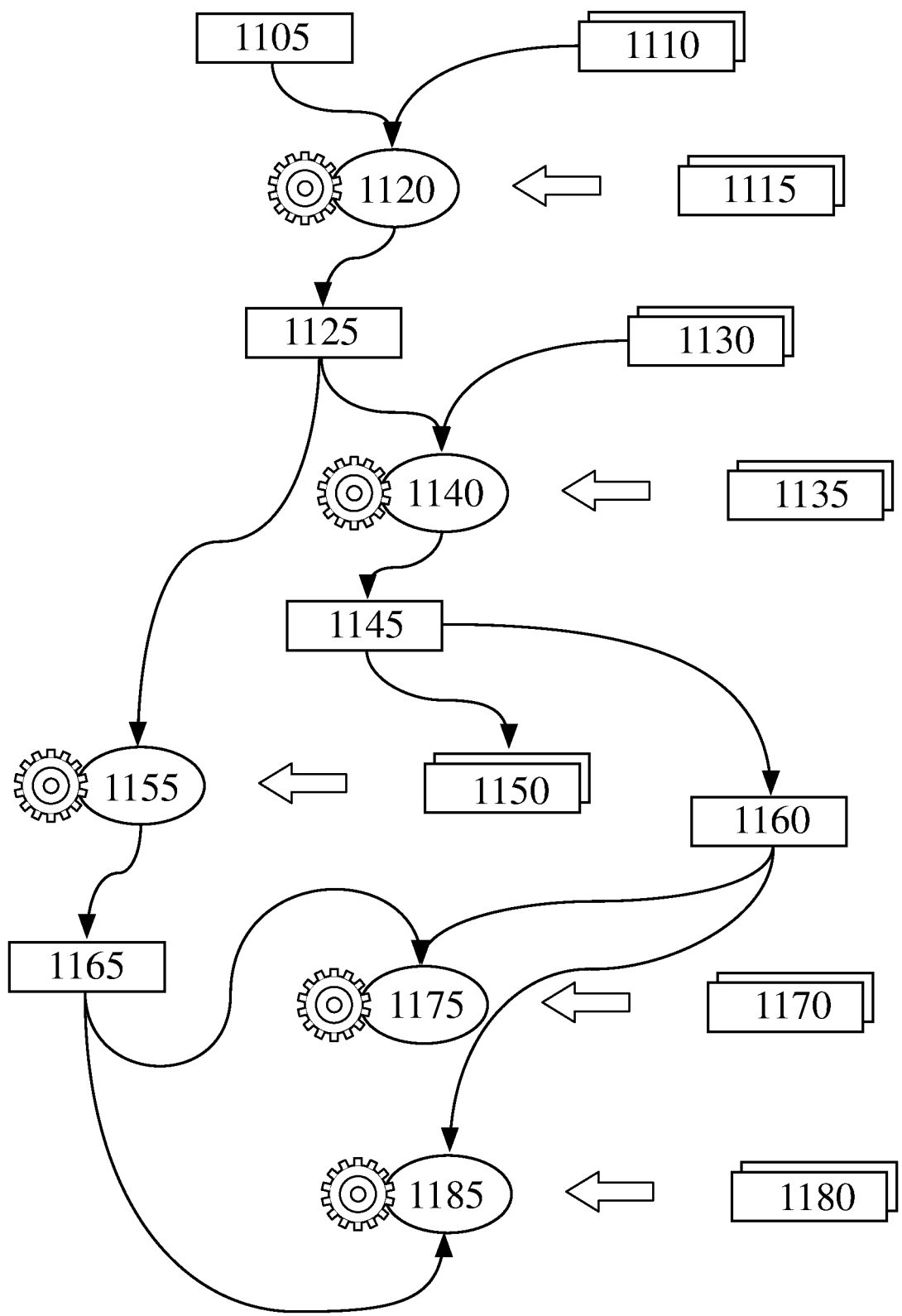
FIG. 5 depicts a flow chart showing the steps of applying various rules to the selected Study, according to an embodiment of the invention.

FIG. 5 is a flow chart showing how the rules are used to create the two Sets of Images shown in FIG. 6. As shown in FIG. 5, a primary Study 1105 which can be manually selected by a user. In step (i) 1120, based on Study Selection Rules 1115 which interrogate parameters in the primary Study 1105 such as DICOM Parameters and Abstract Tags of both the primary Study 1105 and the candidate studies 1110, the Study Selection Rules 1115 can identify additional candidate studies 1110. The second set of studies 1125 which includes the candidate studies 1110 and the primary Study 1105 are available to be loaded into Viewports 1160. In step (ii) 1140, the Protocol Selection Rules 1135 select a Display Protocol 1145 from the Available Display Protocols 1130 based on DICOM Parameters and Abstract Tags present in the second studies 1125. In step (iii) 1155, Image Set Rules 1150 are used to define a plurality of Image Sets 1165 from the second studies 1125. The one or more Viewports 1160 are defined in the Display Protocol 1145. In step (iv) 1175, Viewport Assignment Rules 1170 assign one or more Image Sets 1165 to one or more Viewports 1160. In step (v) 1185, Style Rules 1180 define a rendering style and rendering parameters. In an embodiment of the invention steps (i) through (v) are performed by a server processor running a render server program with an interface shown in FIG. 7 in which the rules (Study Selection Rules 1115, Protocol Selection Rules 1135, Image Set Rules 1150, Viewport Assignment Rules 1170, and the one or more Style Rules 1180) are used to automatically select and display the Image Sets 1165 in the Viewports 1160.

A render server program is described in U.S. application Ser. No. 13/831,967, entitled "Multi-User Mult-GPU Render Server Apparatus and Methods", inventors M. Westerhoff et al, which was filed Mar. 15, 2013, is herein expressly incorporated by reference in its entirety. A method of improving responsiveness is described in U.S. application Ser. No. 13/831,982, entitled "Method and System for Transferring Data to Improve Responsiveness when Sending Large Data Sets", inventors D Stalling et al, which was filed Mar. 15, 2013, is herein incorporated by reference in its entirety.

Study Selection Rules 1115

In an embodiment of the present invention, based on the Study that the user selects for display (primary Study 1105), the system can first apply user defined rules to determine additional studies to be displayed together with the primary Study 1105. Such additional studies can be prior examinations that are relevant for the diagnosis of the current Study, or additional current studies. For example, a PET examination will often be looked at together with a CT examination acquired at the same time. The set of rules are constructed as follows:

Each rule consists of a matching criterion for the primary Study 1105 (primary condition), as well as matching criteria for additional studies (secondary condition). The matching criterion is an expression consisting of operators that allow evaluating the parameters of the Study and comparing them to defined values. The parameters of the Study are any parameters defined by the DICOM standard, such as Study Description, Study Date, Modality, Patient Age, as well as any other parameters that can be derived from the DICOM parameters or from the Study itself, such as number of images, or number of image series. The operators are numeric or string based operators, such as equals, greater than, less than, contains, etc. Expressions can be combined using Boolean operators such as AND, OR, NOT. Operators can also contain more complex expressions, including user defined functions defined in an appropriate programming language, such as JavaScript or VisualBasic.

Once a primary Study 1105 has been selected for display, the primary condition of each rule is evaluated. Those rules that match, i.e., evaluate to "true" for the given primary Study 1105, will then be applied to all other studies that are available for the same patient. Those other studies for which the secondary condition matches will be added to the list of studies to be displayed.

The following rule illustrates the concept. This rule will automatically load prior Chest X-Rays or prior Chest CT if the primary Study 1105 is a Chest X-RAY.
Study Selection Rule 1:
IF (Primary.Dicom.BodyPartExamined="CHEST" and Primary.Dicom.Modality="CR") THEN SELECT other studies for loading WHERE (Other.Dicom.BodyPartExamined="CHEST" and (Other.Dicom.Modality="CR" or Other.Dicom.Modality="CT"))

The rule is expressed in pseudo-code with the primary condition specified in the IF-clause and the secondary condition expressed in the SELECT-clause.
Study Selection Rules: Normalization of DICOM Parameters In an embodiment of the present invention, the rules can normalize DICOM parameters. As described above, a Study Selection Rule can contain arbitrary DICOM parameters. The DICOM standard specifies if a particular parameter is defined on a patient, Study, series, or image level. For example, a Study-level parameter should have the same value in all images of a Study, while a series-level parameter should have the same value in all images of a series. There are two problems related to assuming that this statement is always the case. Firstly, although a Study-level tag should have the same value for all images of a Study this is not always true. Secondly, some parameters are defined on a series- or image-level (e.g. modality is a series-level parameter) and therefore can be unavailable. In both cases it can be unclear what value is to be used when evaluating the rule. The invention described here provides different solutions to this problem.

In an embodiment of the present invention, a first approach is to choose a reference image and to read the value of a particular DICOM parameter from the reference image. The reference image can be: (i) the image that was inserted into the system first, (ii) the image with the oldest image content date, (iii) the image that was inserted into the system last, or (iv) the image with the earliest image content date. The choice of which image is to be chosen as the reference image can be configured for each parameter separately.

In an embodiment of the present invention, a second approach is to only allow original images to be chosen as the reference image. Non-viewable DICOM objects like structured reports, key objects, or presentation states are disregarded, as well as derived images such as secondary capture images or reformatted images.

In an embodiment of the present invention, a third approach is to provide a list of all distinct values that a particular DICOM parameter has in the images of a Study. In a Study Selection Rule one can then check if that list contains a particular value. The example above can then read as follows:

Study Selection Rule 2:
IF (Primary.Dicom.BodyPartExamined="CHEST" and Primary.DiconmList.Modality contains "CR") THEN SELECT other studies for loading WHERE (Other.Dicom.BodyPartExamined="CHEST" and (Other.DiconmList.Modality contains "CR" or Other.DicomList.Modality contains "CT"))

Study Selection Rules: Abstract Tags

In an embodiment of the present invention, the Study Selection Rules 1115 contain other derived parameters such as Abstract Tags that characterize a Study in addition to or instead of DICOM parameters. Abstract tags that are useful within Study Selection Rules 1115 include the following:
  (i) RelativeStudyAge indicates relative age of Study in days compared to primary Study 1105.
  (ii) PriorIndex indicates an index that enumerates all other studies from youngest to oldest.
  (iii) NumImages indicates number of images in Study.
  (iv) NumSeries indicated number of image series in Study.
  (v) Num3DVolumes indicates number of 3D volumes in Study.
  (vi) Num4DSequences indicates number of 4D sequences in Study (e.g. Cardiac CT).
  (vii) HasReport indicates a flag that indicates if a report is available for a Study.
  (viii) HasThinSliceVolumes indicates whether the study has at least one set of images that form a true 3D volume, i.e. a sufficiently large number of equidistant slices (the exact number can be user configurable, e.g. 30 would be a common choice) and a sufficiently small spacing between two consecutive slices to guarantee an isotropic (or close to isotropic) (again, this parameter can be user defined, values between 1 mm and 3 mm are common thresholds for CT and MR examinations).

For example, a rule that applies to a Mammogram Study and that selects at maximum three prior Mammogram studies no older than five years can read as follows:

Study Selection Rule 3:
IF (Primary.Dicom.Modality="MG" THEN SELECT other studies for loading WHERE (Other.Dicom.Modality="MG" and Other.Abstract.PriorIndex<=3 and Other.Abstract.RelativeStudyAge<5*365)

Protocol Selection Rules 1135

In an embodiment of the present invention, once the studies to be displayed are determined as described above, a suitable display protocol can be selected. This is done using matching rules. Each matching rule consists of conditions that are applied to the primary and other studies to be loaded. Like in Study Selection Rules 1115, protocol selection rules may contain DICOM parameters (either taken from a reference image or provided as a list of distinct values gathered from all images of a study), as well as abstract tags and user-defined functions. Each matching rule has a score and an associated display protocol.

In an embodiment of the present invention, all matching rules are evaluated and the display protocol of the matching rule that evaluates to true can be selected. If multiple matching rules evaluate to true, the one with the highest score can be selected.

The following example rule illustrates a matching rule that can apply for PET/CT studies of the abdomen to select a protocol named "StandardPetCTProtocol1" with a score of 10.

Protocol Selection Rule 1:
IF (Primary.Dicom.BodyPartExamined="ABDOMEN" and Primary.Dicom.Modality="CT" and Exists(Other1) and Other1.Dicom.Modality="PET") THEN SELECT "StandardPetCTProtocol1" with score=10

In an embodiment of the present invention, the rule is expressed in pseudo-code with the matching condition specified in the IF-clause and the chosen protocol specified by the SELECT.

Image Set Rules 1150

In an embodiment of the present invention, once a display protocol is selected, further rules defined within the protocol are evaluated. The next step comprises creation of so-called image sets. An image set consists of images that are logically grouped together. Usually, an image set is represented by a single preview icon in the application. It is an image set that is loaded into a viewer or tiled viewer. Note that DICOM series also represent a logical grouping of images. However, often DICOM series are not well suited for hanging of images and viewing. For example, in Mammography a single DICOM series may contain images of both left and right breast, in MRI it may contain both T1 and T2 images, or in CT it may contain both a localizer image (topogram) and a 3D image stack. In all these cases the DICOM series can be split into different logical image sets. On the other hand, multiple DICOM series may represent the phases of a single 4D cardiac data set. In this case all those series can be joined into a single logical image set. Displaying volumetric images obtained from digital breast tomosynthesis is disclosed in U.S. patent application Ser. No. 15/218,972 titled 'Apparatus and Method for Visualizing Digital Breast Tomosynthesis and Other Volumetric Images' filed Jul. 25, 2016, the specification and drawings of which are herein expressly incorporated by reference in their entirety.

Thus the creation of image sets based on rules is a key component of the rule-based display system, specifically for the more advanced rendering techniques. For example, the rules-based display system is used to create image sets that are very similar to the rules described above in Study Selection Rules 1115 and Protocol Selection Rules 1135 sections. A rule is a Boolean expression that can contain DICOM parameters, abstract tags, or used-defined functions that are based on the DICOM parameters, abstract tags, or used-defined functions. Image set rules however, are applied to all images of a study that was selected for loading (and not to the study itself). Image-level parameters thus represent no problem and do not need to be normalized or otherwise treated specially. All images that match an image-set rule are grouped into a respective image set.

In an embodiment of the present invention, the following rule (expressed in pseudo-code) collects all images of a current CT study:

Image Set Rule 1:
IF (Dicom.Modality="CT" and Abstract.PriorIndex=0) THEN CREATE image set with ID 1

In an embodiment of the present invention, the resulting image sets can be assigned IDs or names that allow for referencing the image sets later in layout and display set rules. In the above example an image set with ID 1 was defined. If no image matches an image set rule, no such corresponding image set will be created.

Image Set Rules: Sorting

In an embodiment of the present invention, the order of images within an image set is an important aspect. It determines how images are shown when the user browses through the image set or how images are distributed into the tiles of a tiled viewer. In one embodiment of the present invention, in order to specify image sorting, the image set rules can contain an ordered list of sorting criteria. All images that are matched by a rule are sorted according to those criteria.

For example, the following rule collects all images of a current CT study and sorts them according to DICOM series number at first and DICOM instance/image number at second.

Image Set Rule 2:
IF (Dicom.Modality="CT" and Abstract.PriorIndex=0)
THEN CREATE image set with ID 1
    SORTED BY Dicom.SeriesNumber ORDER:=ascending
    SORTED BY Dicom.InstanceNumber ORDER:=ascending Image Set Rules: Splitting In an embodiment of the present invention, sorting criteria can be extended by a split flag. With the split flag it is possible to create multiple image sets from a single image set rule. When the value of a sorting criterion with split flag set to true changes, sub-sequent images are automatically inserted into a new image set. The resulting image sets are automatically enumerated by a sub-level ID.

For example, the following rule essentially creates image sets that correspond to DICOM series, because all images with different series number will be split into different sets:

Image Set Rule 3:
IF (Dicom.Modality="CT" and Abstract.PriorIndex=0)
THEN CREATE image set with ID 1.x
    SORTED BY Dicom.SeriesNumber ORDER:=ascending SPLIT:=true
    SORTED BY Dicom.InstanceNumber ORDER:=ascending SPLIT:=false In applications where a CT has been measured, it can happen that a study contains both a soft-kernel series and a hard kernel series and both series have the same series number. In order to separate the images into different image sets the above rule can be extended by the following:

Image Set Rule 4:
IF (Dicom.Modality="CT" and Abstract.PriorIndex=0)
THEN CREATE image set with ID 1.x
    SORTED BY Condition.CTSoftTisseKernel SPLIT:=true
    SORTED BY Dicom.SeriesNumber ORDER:=ascending SPLIT:=true
    SORTED BY Dicom.InstanceNumber ORDER:=ascending SPLIT:=false Here, Condition.CTSoftTissueKernel denotes a user-defined Boolean condition that tests whether an image has a CT soft-tissue kernel. The actual implementation of this condition can for example evaluate the manufacturer (which is encoded in a DICOM parameter). Depending on its value the rule can evaluate further parameters to find out if an image was reconstructed using a soft-tissue kernel or not. Since this Boolean condition was used as a sorting criterion with the split flag set to true, all non-soft-kernel images can be put into an image set with ID 1.1 and all soft-kernel images can be put into an image set with ID 1.2 (unless the image set is further split and IDs like 1.3 or 1.4 are created).

Image Set Rules: More Abstract Tags

In an embodiment of the present invention, additional abstract tags are used in image set rules. One example is a tag that identifies whether an image has already been put into an image set. In principle, a single image can be put into multiple image sets, but sometimes this should be avoided. This can be achieved by evaluating image set rules in a pre-defined order and introducing an abstract tag AlreadyReferenced.

For example, in CT study that has a localizer image and a 3D image stack both stored in one DICOM series, one may want to create an image set, one for the localizer and one for the 3D image stack. Accordingly, the image set rules are defined as follows:

Image Set Rule 5 (Localizer):
IF (Dicom.Modality="CT" and Condition.IsLocalizer=true)
THEN CREATE image set with ID 1
    SORTED BY Dicom.SeriesNumber ORDER:=ascending SPLIT:=true
    SORTED BY Dicom.InstanceNumber ORDER:=ascending SPLIT:=false Image Set Rule 6 (Images):
IF (Dicom.Modality="CT" and Abstract.AlreadyReferenced=false)
THEN CREATE image set with ID 2
    SORTED BY Dicom.SeriesNumber ORDER:=ascending SPLIT:=true
    SORTED BY Dicom.InstanceNumber ORDER:=ascending SPLIT:=false Here Condition.IsLocalizer is a user-defined condition that returns true if an image is a localizer image, and false otherwise. In an embodiment of the present invention, Rule 1 is applied first. Therefore the localizer image is put into a separate image set with ID 1. Next rule 2 is applied. This rule can match for all CT images including the localizer image. However, because AlreadyReferenced=false is specified, the localizer image is skipped and not placed into image set 2.

In an embodiment of the present invention, the creation of the image sets based on rules is a key component of the efficient rules based display, specifically for the more advanced rendering techniques. For example rules can be used to identify sets of 2D images that together form a 3D volume.

Viewer Assignment Rules

In another embodiment of the present invention, a display protocol defines multiple viewers, each with one or more tiles, i.e., viewports. To each viewer one or more image sets can be assigned based on Viewer Assignment Rules that are similar to the protocol section rules described herein. Viewer Assignment Rules are defined in the display protocol. The rules determine which image set shall be initially shown in a viewer. In case multiple image sets are assigned to a viewer, the one with the highest score is chosen. Afterwards users may cycle quickly through the remaining image sets using dedicated tools (Previous/Next Image Set), or pick another image set from a special image set menu.

Like the other rule types Viewer Assignment Rules contain Boolean expressions of DICOM parameters, abstract tags, or user-defined conditions based on DICOM parameters, or abstract tags. In many cases it is sufficient to specify the image sets to be assigned to a viewer by their image set ID instead of evaluating the underlying DICOM parameters and abstract tags again. Therefore, the image set ID is simply set as a separate abstract tag. In the following example the two rules load image sets with the IDs 1 and 2 into a viewer, but assign ID 1 a higher score so that this image set is initially visible (provided such an image set exists):

Viewer Assignment Rule 1:
IF (EXISTS ImageSet[1])
THEN Viewport[0].AddImageSet(ID=1, score=10)
Viewer Assignment Rule 2:
IF (EXISTS ImageSet[2])

THEN
Viewport[0].AddImageSet(ID=2, score=5)

In an embodiment of the present invention, viewer assignment rules are applied to image sets. Thus there is a possible conflict regarding ambiguous image-level and series-level tags. This conflict is resolved in the same way as described herein in the Normalization of DICOM Parameters section. This means that values of DICOM parameters, but also abstract tags, are automatically taken from some reference image. Alternatively, for all DICOM parameters a list of distinct values occurring in all images of the image set can be used in an assignment rule.

Style Rules

In one embodiment of the present invention, there is a final set of rules that specify the rendering style and other rendering parameters to be used when showing a particular image set. For example, for a CT Angiogram study, often a volume rendering style display (VRT) is desired, whereas for a study looking for lung nodules a maximum intensity projection (MIP) of 20 mm slabs may be desired. Style rules, that can be user specific, allow driving that automatically. The rules can use the same parameters as discussed above, as well as the existence or absence of certain image sets.

In one embodiment of the present invention, the system uses a global, ordered list of style rules that is evaluated independently for each viewer and each image set loaded into a viewer. An abstract tag DisplaySetID is provided that allows formulating style rules for a specific viewer or group of viewers.

Parameters driven by Style Rules include the following:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements.

The following is an example of a style rule that activates inverse 3D MIP rendering in all viewers with a DisplaySetID between 101 and 104, provided a PET data set is loaded into those viewers (modality PT, i.e., positron emission tomography). Also, an automatic window/level setting is used that is computed from the histogram of the image set (the 2% lowest values are all mapped to white, and the 2% highest values are all mapped to black):

Style Rule 1:
IF (Abstract.DisplaySetID>100 and
    Abstract.DisplaySetID<105 and
    Dicom.Modality="PT")
THEN SET
RenderingStyle:="3D MIP"
Inverse:=true
DataWindow:="2% 98%"

The following is another example of a different style rule that always causes the image set with image set ID 200 to be displayed in MPR mode using 20 mm thick slices, with a window/level as specified in the DICOM parameters, and with a zoom factor so that the whole viewer window is filled out. The rule is:

Style Rule 2:
IF (Abstract.ImageSetID=200)
THEN SET
RenderingStyle:="MPR"
SliceThickness:="20"
DataWindow:="DICOM1"
ZoomFactor:="FitToWindow"

Summary of Rule Types

Table I summarizes all types of rules that are applied in the rule-base display system:

TABLE I

| Rule Type | Applies to | Normalized Parameters | Defined where |
|---|---|---|---|
| Study Selection Rule | Studies | yes | globally |
| Protocol Selection Rule | Studies | yes | globally |
| Image Set Rule | Images | not required | protocol |
| Viewer AssignmentRule | Image Sets | yes | globally, protocol |
| Style Rule | Image Sets | yes | globally, protocol |

Described above are methods and systems for implementing a rule derived basis to display image sets. The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

Example Shown in FIG. 6

An example of how these aspects can be combined is shown in FIG. 6. In the example the user has selected a CT examination of the abdomen. The following rules have been used to determine that a recent X-Ray of the chest is relevant and shall be displayed as well: IF (Primary.Dicom.BodyPartExamined="ABDOMEN" and Primary.Dicom.Modality="CT") THEN SELECT other studies for loading WHERE (Other.Dicom.BodyPartExamined="ABDOMEN" OR Other.Dicom.BodyPartExamined="CHEST") and (Other.Dicom.Modality="CR" or Other.Dicom.Modality="CT") AND Other.RelativeStudyAge<"90 days"

From this rule, a hanging protocol can be selected. In the example the protocol selection rules determine that the CT study is a thin slice CT study (i.e. that it has image series that form a 3D volume with sufficient resolution in all directions to display volume rendering or non-axial slices in a meaningful way). Furthermore the example rule determines that this is a study with enhanced vasculature, by looking for the key words "contrast" or "angio" in the study description. The display protocol selection rule that applies here and select the protocol CTThinSliceVesselWithPrior can read IF (Primary.Dicom.BodyPartExamined="ABDOMEN" and Primary.Dicom.Modality="CT" and Primary.Abstract.H- asThinSliceVolumes and (Primary.Dicom.StudyDescription containsAnyOf "contrast, angio" and exists Other1 THEN SELECT "CTThinSliceVesselWithPrior" with score=10

From this image sets are generated using Image Set Rules:
IF (Dicom.Modality="CT" and Abstract.PriorIndex=0 and Condition.IsPartOfThinSliceVolume and Condition.CTSoft-TisseKernel)
THEN CREATE image set with ID 1.x
    SORTED BY Abstract.NumberOfSlicesInVolume ORDER:=descending SPLIT:=true
    SORTED BY Dicom.SeriesNumber ORDER:=ascending SPLIT:=true
    SORTED BY Dicom.Abstract.VolumeIndex ORDER:=ascending SPLIT:=true
    SORTED BY Dicom.Abstract.SlicePosition ORDER:=ascending SPLIT:=false This rule will actually form sets from images that contain images that are part of a ThinSliceVolume and that have been reconstructed with a "soft tissue" kernel. Given the protocol selection rule has specifically matched for just CT studies, the conditions Dicom.Modality="CT" and Abstract.PriorIndex=0 are actually redundant, but could be useful if a different selection rule was used.

The images will first be sorted by the size of the volume of which they are part (Abstract.NumberOfSlicesInVolume), then by DICOM series. The split parameter in this case will ensure that an image set contains images from on series only. A DICOM series can sometimes contain multiple non-consecutive volumes. The abstract tag VolumeIndex will then indicate for each image, which of those volumes it is part of. If a series contains only one volume, then this will be "1" for all images in the series. The split=true in this part of the rule would result in a separate image set for each of those volumes. Finally, within each volume, the images are ordered by slice position, but not split. This way we end up with one image set for each soft kernel thin slice volume, the largest volume being the first image set (ID 1.1). This ID will be used further in subsequent rules.

The rule to form an image set from any CR prior study in this example is much simpler:
IF (Dicom.Modality="CR" and Abstract.PriorIndex=1)
THEN CREATE image set with ID 10
    SORTED BY Dicom.SeriesNumber ORDER:=ascending SPLIT:=false
    SORTED BY Dicom.InstanceNumber ORDER:=ascending SPLIT:=false This creates one image set with ID=10 containing all images for the first prior study, if that is a CR.

In practice, additional rules, such as Image Set Rule 5 and 6 (see above) will be used to collect the remaining images of the primary Study 1105. The remaining images are not shown in the layout depicted in the example FIG. 6.

The Display Protocol 1145 contains multiple layouts. The one shown in FIG. 6 is defined as follows:
DEFINE Layout {
  ID="Layout5";
  NAME="+PlainFilm"
  Viewports {
  {ID=50, Geometry="(0,0)-(0.25,0.5)"},
  {ID=51, Geometry="(0.25,0)-(0.5,0.5)"},
  {ID=52, Geometry="(0,0.5)-(0.25,1)"},
  {ID=53, Geometry="(0.25,0.5)-(0.5,0.5)"},
  {ID=54, Geometry="(0.5,0)-(1,1)", Style="2D" }
  }
}

In this example the geometry is defined in a coordinate system having the origin in the upper left corner of the screen with the x axis pointing to the right and the y axis pointing down. Please note how parameters of the viewers can be set in the layout definition. Parameters can also be set or overridden in the assignment and style rules, as will be explained next.

In this example, viewer assignment and style rules are as follows:
IF ImageSetExists (1.1) and ImageSetExists(10) THEN
  SHOW_LAYOUT Layout5 WITH
  Viewport[0].AddImageSet(1.1)
    Viewport [0].Style="VRT(diffuse)"
    Viewport [0].Colormap="CTAngioSoftTissue"
  Viewport [1,2,3].AddImageSet(1.1)
    Viewport [1,2,3].Style="MPR"
    Viewport [1,2,3].DataWindow="DICOM1"
  Viewport [1].oriantation="axial"
  Viewport [2].oriantation="sagittal"
  Viewport [3].oriantation="coronal"
  Viewport [4].AddImageSet(10)
  IF (ImageSet[10].Dicom.Columns>1024) THEN
    Viewport[4].Zoom="FitToWindow"
  ELSE
    Viewport[4].Zoom="1:1"

In this particular example, the rule to select the layout is rather simple: It is shown if the two image sets used exist. This is because the criteria to construct these images sets have been rather specific. As will be appreciated, the proposed system gives this type of flexibility.

Aspects of the Invention

Some aspects of this invention include methods of displaying one or more Sets of Images comprising the steps of:
  a. selecting a primary Study;
  b. selecting one or more Study Selection Parameters based on the primary Study;
  c. selecting one or more Study Selection Rules based on the one or more Study Selection Parameters;
  d. selecting one or more Sets of Images from a plurality of images based on the one or more Study Selection Rules;
  e. selecting one or more Display Protocol Selection Parameters based on the one or more Sets of Images selected;
  f. selecting one or more Display Protocol Selection Rules based on the one or more Display Protocol Selection Parameters;
  g. selecting one or more Display Parameters using the one or more Display Protocol Selection Rules; and
  h. displaying the one or more Sets of Images according to the Display Parameters.

Additional aspects include methods one or more Display Parameter are selected from the group consisting of Image Set Selection Parameters and View and Viewport Selection Parameters.

Further aspects include methods where the one or more Display Parameters are selected from the group consisting of Image Set Selection Rules, View and Viewport Selection Rules, and Display Protocol Selection Rules.

Yet further aspects include methods where the step of identifying one or more Image Set Selection Rules is based on the one or more Image Set Selection Parameters.

Still further aspects include methods where the step of selecting one or more Viewpoint Selection Rules is based on one or more View and Viewport Selection Parameters.

Other aspects include methods where the step of displaying the one or more Sets of Images is based on one or more Display Protocol Selection Rules, one or more Image Set Selection Rules, and one or more View and Viewport Selection Rules.

Still other aspects include methods where one or more of the Study Selection Parameters are selected from the group consisting of DICOM parameters and Abstract Tags.

Other aspects include methods where one or more of the Display Protocol Selection Parameters are selected from the group consisting of DICOM parameters and Abstract Tags.

Additional aspects include methods where one or more of the Image Set Selection Parameters are selected from the group consisting of DICOM parameters and Abstract Tags.

Further aspects include methods where one or more of the View and Viewport Selection Parameters are selected from the group consisting of DICOM parameters and Abstract Tags.

More aspects include methods where one or more Study Selection Parameters are derived from a single reference image.

Still more aspects include methods where one or more Study Selection Parameters are derived from a single reference image DICOM Parameters.

Yet other aspects include methods where one or more Display Protocol Selection Parameters are derived using a list of all values of a DICOM parameter occurring in any of the one or more Sets of Images.

Alternative aspects include methods where the one or more View and Viewport Selection Rules contain protocols for one or more Viewports displaying images as 2D.

Other alternative aspects include methods where the one or more View and Viewport Selection Rules contain protocols for one or more Viewports displaying images in a 3D rendering mode.

Further alternative aspects include methods where one or more Study Selection Parameters include one or more Abstract Tags selected from the group consisting of RelativeStudyAge, PriorIndex. NumImages, NumSeries, Num3DVolumes, Num4DSequences and HasReport.

In other aspects, this invention includes methods where one or more View and Viewport Selection Rules include one or more Abstract Tags selected from the group consisting of Image Sets to be displayed, Rendering Style, Additional image sets for image fusion, Image Alignment, Colormap/Transfer Function, Slice Thickness, Zoom Factor, Camera position, Camera orientation and Labels/Overlay elements.

In still other aspects, this invention includes methods further comprising the steps of:
receiving one or more Sets of Images based on the Study Selection Rules;
selecting one or more Image Set Selection Parameters;
selecting one or more Image Set Selection Rules based on the one or more Image Set Selection Parameters; and
displaying the one or more Sets of Images based on the Display Protocol Selection Rules and the Image Set Selection Rules.

In another aspect, this invention includes methods of displaying one or more Sets of Images comprising the steps of:
selecting one or more Study Selection Parameters;
selecting or more Study Selection Rules based on the one or more Study Selection Parameters;
receiving one or more Sets of Images based on the Study Selection Rules;
selecting one or more Display Protocol Selection Parameters based on the one or more Sets of Images selected;
selecting one or more Display Protocol Selection Rules based on the one or more Display Protocol Selection Parameters; and
displaying the one or more Sets of Images based on the Display Protocol Selection Rules.

Another aspect of this invention includes methods of displaying images comprising the steps of:
a. selecting one or more Study Selection Parameters;
b. selecting Study Selection Rules based on the one or more Study Selection Parameters;
c. receiving one or more images based on the Study Selection Rules;
d. selecting one or more Display Protocol Selection Parameters based on the one or more images selected;
e. selecting Display Protocol Selection Rules based on the one or more Display Protocol Selection Parameters;
f. selecting one or more Image Set Selection Parameters;
g. selecting Image Set Selection Rules based on the one or more Image Set Selection Parameters;
h. selecting one or more View and Viewport Selection Parameters;
i. selecting View and Viewport Selection Rules based on the one or more View and Viewport Selection Parameters; and
j. displaying the one or more images based on the Display Protocol Selection Rules, the Image Set Selection Rules and the View and Viewport Selection Rules.

Other aspects of the invention include methods where the Study Selection Rule is:
IF (Primary.Dicom.BodyPartExamined="CHEST" and Primary.Dicom.Modality "CR")
THEN SELECT other studies for loading WHERE (Other.Dicom. BodyPartExamined="CHEST" and (Other.Dicom.Modality="CR" or Other.Dicom.Modality="CT")).

In another aspect, this invention includes methods where the Study Selection Rule is:
IF (Primary.Dicom.BodyPartExamined="CHEST" and Primary.DiconmList.Modality contains "CR") THEN SELECT other studies for loading WHERE (Other.Dicom.BodyPartExamined="CHEST" and (Other.DiconmList.Modality contains "CR" or Other.DicomList.Modality contains "CT")).

In other aspects, this invention includes methods where the Study Selection Rule is:
IF (Primary.Dicom.Modality="MG" THEN SELECT other studies for loading WHERE (Other.Dicom.Modality="MG" and Other.Abstract.PriorIndex<=3 and Other.Abstract.RelativeStudyAge<5*365).

In yet another aspect, this invention includes methods where the Protocol Selection Rule is:
IF (Primary.Dicom.BodyPartExamined="ABDOMEN" and Primary.Dicom.Modality="CT" and Exists (Other1) and Other1.Dicom.Modality="PET") THEN SELECT "StandardPetCTProtocol1" with score=10.

In aspects of the invention, methods include an Image Set Rule:
IF (Dicom.Modality="CT" and Abstract.PriorIndex=0) THEN CREATE image set with ID 1.

Additionally, other aspects include methods where the Image Set Rule is:
IF (Dicom.Modality="CT" and Abstract.PriorIndex=0) THEN CREATE image set with ID 1
SORTED BY Dicom.SeriesNumber ORDER:=ascending SORTED BY Dicom.InstanceNumber ORDER:=ascending.

Still other aspects include methods where the Image Set Rule is:
IF (Dicom.Modality="CT" and Abstract.PriorIndex=0)
THEN CREATE image set with ID 1.x
SORTED BY Dicom.SeriesNumber ORDER:=ascending SPLIT:=true
SORTED BY Dicom.InstanceNumber ORDER:=ascending SPLIT:=false.

Moreover, other aspects include methods where the Image Set Rule is:
IF (Dicom.Modality="CT" and Abstract.PriorIndex=0)
THEN CREATE image set with ID 1.x
SORTED BY Condition.CTSoftTisseKernel SPLIT:=true
SORTED BY Dicom.SeriesNumber ORDER:=ascending SPLIT:=true
SORTED BY Dicom.InstanceNumber ORDER:=ascending SPLIT:=false.

Yet other aspects include methods where the Image Set Rule (Localizer) is:
IF (Dicom.Modality="CT" and Condition.IsLocalizer=true)
THEN CREATE image set with ID 1
SORTED BY Dicom.SeriesNumber ORDER:=ascending SPLIT:=true
SORTED BY Dicom.InstanceNumber ORDER:=ascending SPLIT:=false.

Other aspects of the methods of this invention include an Image Set Rule (Images):
IF (Dicom.Modality="CT" and Abstract.AlreadyReferenced=false)
THEN CREATE image set with ID 2
SORTED BY Dicom.SeriesNumber ORDER:=ascending SPLIT:=true
SORTED BY Dicom.InstanceNumber ORDER:=ascending SPLIT:=false.

Yet other aspects of the methods of this invention include using Image Set Rule (Images):
IF (Dicom.Modality="CT" and Abstract.AlreadyReferenced=false)
THEN CREATE image set with ID 2
SORTED BY Dicom.SeriesNumber ORDER:=ascending SPLIT:=true
SORTED BY Dicom.InstanceNumber ORDER:=ascending SPLIT:=false.

Additionally, other aspects include methods where the Display Parameters include Viewer Assignment Rule:
IF (Abstract.ImageSetID=1)
THEN SELECT image set with score=10.

Yet further aspects include methods where the Display Parameters include a Viewer Assignment Rule:
IF (Abstract.ImageSetID=2)
THEN SELECT image set with score=5.

Additional aspects include methods further comprising a Viewer Assignment Rule:
IF (Abstract.ImageSetID=2)
THEN SELECT image set with score=5.

In other aspects of this invention, methods include one or more Study Selection Rules comprising one or more Abstract Tags selected from the group consisting of:
(i) RelativeStudyAge indicates relative age of Study in days compared to primary Study 1105.
(ii) PriorIndex indicates an index that enumerates all other studies from youngest to oldest.
(iii) NumImages indicates number of images in Study.
(iv) NumSeries indicated number of image series in Study.
(v) Num3DVolumes indicates number of 3D volumes in Study.
(vi) Num4DSequences indicates number of 4D sequences in Study (e.g. Cardiac CT).
(vii) HasReport indicates a flag that indicates if a report is available for a Study.
(viii) IsThinSliceVolume.

Aspects of methods also include a step of displaying including use of an Abstract Tag DisplaySetID.

Other aspects of methods include Abstract Tag DisplaySetID having a Style Rule selected from the group consisting of:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements.

Still other methods include steps where the Style Rule is:
IF (Abstract.DisplaySetID>100 and
Abstract.DisplaySetID<105 and
Dicom.Modality="PT")
THEN SET
RenderingStyle:="3D MIP"
Inverse:=true
DataWindow:="2% 98%".

Other aspects of methods include use of a Style Rule:
IF (Abstract.ImageSetID=200)
THEN SET
RenderingStyle:="MPR"
SliceThickness:="20"
DataWindow:="DICOM1"
ZoomFactor:="FitToWindow", Another aspect of the present invention is a method of displaying one or more Sets of Images comprising the steps of:
selecting one or more Study Selection Parameters;
identifying one or more Study Selection Rules based on the one or more Study Selection Parameters;
selecting one or more Sets of Images from a plurality of images based on the one or more Study Selection Rules;
selecting one or more Display Protocol Selection Parameters based on the one or more Sets of Images selected;
identifying one or more Display Protocol Selection Rules based on the one or more Display Protocol Selection Parameters;
using the one or more Display Protocol Selection Rules to select one or more Display Parameters; and
displaying the one or more Sets of Images according to the Display Parameters.

Still other aspects of methods of displaying one or more Sets of Images comprising the steps of:
selecting one or more Study Selection Parameters;
selecting Study Selection Rules based on the one or more Study Selection Parameters;
selecting one or more Sets of Images based on the Study Selection Rules;

selecting one or more Display Protocol Selection Parameters based on the one or more Sets of Images selected;
selecting Display Protocol Selection Rules based on the one or more Display Protocol Selection Parameters;
selecting one or more Image Set Selection Parameters;
selecting Image Set Selection Rules based on the one or more Image Set Selection Parameters;
selecting one or more View and Viewport Selection Parameters;
selecting View and Viewport Selection Rules based on the one or more View and Viewport Selection Parameters; and
displaying the one or more Sets of Images based on the Display Protocol Selection Rules, the Image Set Selection Rules and the View and Viewport Selection Rules.

In systems of this invention, aspects include system for displaying one or more Sets of Images comprising:
one or more digital data processors for carrying out the steps including:
selecting one or more Study Selection Parameters;
selecting one or more Study Selection Rules based on the one or more Study Selection Parameters;
receiving one or more Sets of Images based on the Study Selection Rules;
selecting one or more Display Protocol Selection Parameters based on the one or more Sets of Images selected;
selecting Display Protocol Selection Rules based on the one or more Display Protocol Selection Parameters;
selecting one or more Image Set Selection Parameters;
selecting one or more Image Set Selection Rules based on the one or more Image Set Selection Parameters;
selecting one or more View and Viewport Selection Parameters;
selecting View and Viewport Selection Rules based on the one or more View and Viewport Selection Parameters; and
graphics resources for displaying the one or more Sets of Images based on one or more of Display Protocol Selection Rules, Image Set Selection Rules, the View and Viewport Selection Rules, and Viewer Assignment Rules.

Additional system aspects include Sets of Images comprising:
one or more digital data processors for carrying out the steps according to any of the above described methods aspects;
and graphics resources for displaying the one or more Sets of Images.

In an embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another embodiment of the invention, a method of displaying images comprises the steps of:
selecting one or more Study Selection Parameters;
identifying a Study Selection Rule based on the one or more Study Selection Parameters, where the Study Selection Rule is:
IF (Primary.Dicom.BodyPartExamined="CHEST" and Primary.Dicom.Modality="CR")
THEN SELECT other studies for loading WHERE (Other.Dicom. BodyPartExamined="CHEST" and (Other.Dicom.Modality="CR" or Other.Dicom.Modality="CT"));
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In an alternative embodiment of the invention, a method of displaying images comprises the steps of:
selecting one or more Study Selection Parameters;
identifying a Study Selection Rule based on the one or more Study Selection Parameters, where the Study Selection Rule is:
IF (Primary.Dicom.BodyPartExamined="CHEST" and Primary.DiconmList.Modality contains "CR") THEN SELECT other studies for loading WHERE (Other.Dicom.BodyPartExamined="CHEST" and (Other.DiconmList.Modality contains "CR" or Other.DicomList.Modality contains "CT"));
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another alternative embodiment of the invention, a method of displaying images comprises the steps of:
selecting one or more Study Selection Parameters;
identifying a Study Selection Rule based on the one or more Study Selection Parameters, where the Study Selection Rule is:

IF (Primary.Dicom.Modality="MG" THEN SELECT other studies for loading WHERE (Other.Dicom.Modality="MG" and Other.Abstract.PriorIndex<=3 and Other.Abstract.RelativeStudyAge<5*365);

receiving one or more images based on the Study Selection Rules;

selecting one or more Display Protocol Selection Parameters based on the one or more images selected;

identifying Display Protocol Selection Rules based on the one or more Display Protocol Selection Parameters;

selecting one or more Image Set Selection Parameters;

identifying Image Set Selection Rules based on the one or more Image Set Selection Parameters;

selecting one or more View and Viewport Selection Parameters;

identifying View and Viewport Selection Rules based on the one or more View and Viewport Selection Parameters; and displaying the one or more images based on the Display Protocol Selection Rules, the Image Set Selection Rules and the View and Viewport Selection Rules.

In an embodiment of the invention, a method of displaying images comprises the steps of:

selecting one or more Study Selection Parameters;

identifying Study Selection Rules based on the one or more Study Selection Parameters;

receiving one or more images based on the Study Selection Rules;

selecting one or more Display Protocol Selection Parameters based on the one or more images selected;

identifying a Display Protocol Selection Rule based on the one or more Display Protocol Selection Parameters, where the Display Protocol Selection Rule is:

IF (Primary.Dicom.BodyPartExamined="ABDOMEN" and Primary.Dicom.Modality="CT" and Exists (Other1) and Other1.Dicom.Modality="PET") THEN SELECT "StandardPetCTProtocol1" with score=10;

selecting one or more Image Set Selection Parameters;

identifying Image Set Selection Rules based on the one or more Image Set Selection Parameters;

selecting one or more View and Viewport Selection Parameters;

identifying View and Viewport Selection Rules based on the one or more View and Viewport Selection Parameters; and displaying the one or more images based on the Display Protocol Selection Rules, the Image Set Selection Rules and the View and Viewport Selection Rules.

In a further embodiment of the invention, a method of displaying images comprises the steps of:

selecting one or more Study Selection Parameters;

identifying Study Selection Rules based on the one or more Study Selection Parameters;

receiving one or more images based on the Study Selection Rules;

selecting one or more Display Protocol Selection Parameters based on the one or more images selected;

identifying Display Protocol Selection Rules based on the one or more Display Protocol Selection Parameters;

selecting one or more Image Set Selection Parameters;

identifying Image Set Selection Rules based on the one or more Image Set Selection Parameters, where the Image Set Selection Rule is:

IF (Dicom.Modality="CT" and Abstract.PriorIndex=0) THEN CREATE image set with ID 1;

selecting one or more View and Viewport Selection Parameters;

identifying View and Viewport Selection Rules based on the one or more View and Viewport Selection Parameters; and displaying the one or more images based on the Display Protocol Selection Rules, the Image Set Selection Rules and the View and Viewport Selection Rules.

In an additional embodiment of the invention, a method of displaying images comprises the steps of:

selecting one or more Study Selection Parameters;

identifying Study Selection Rules based on the one or more Study Selection Parameters;

receiving one or more images based on the Study Selection Rules;

selecting one or more Display Protocol Selection Parameters based on the one or more images selected;

identifying Display Protocol Selection Rules based on the one or more Display Protocol Selection Parameters;

selecting one or more Image Set Selection Parameters;

identifying Image Set Selection Rules based on the one or more Image Set Selection Parameters, where the Image Set Selection Rule is:

IF (Dicom.Modality="CT" and Abstract.PriorIndex=0) THEN CREATE image set with ID 1
  SORTED BY Dicom.SeriesNumber ORDER:=ascending
  SORTED BY Dicom.InstanceNumber ORDER:=ascending;

selecting one or more View and Viewport Selection Parameters;

identifying View and Viewport Selection Rules based on the one or more View and Viewport Selection Parameters; and displaying the one or more images based on the Display Protocol Selection Rules, the Image Set Selection Rules and the View and Viewport Selection Rules.

In another embodiment of the invention, a method of displaying images comprises the steps of:

selecting one or more Study Selection Parameters;

identifying Study Selection Rules based on the one or more Study Selection Parameters;

receiving one or more images based on the Study Selection Rules;

selecting one or more Display Protocol Selection Parameters based on the one or more images selected;

identifying Display Protocol Selection Rules based on the one or more Display Protocol Selection Parameters;

selecting one or more Image Set Selection Parameters;

identifying Image Set Selection Rules based on the one or more Image Set Selection Parameters, where the Image Set Selection Rule is:

IF (Dicom.Modality="CT" and Abstract.PriorIndex=0) THEN CREATE image set with ID 1.x
  SORTED BY Dicom.SeriesNumber ORDER:=ascending SPLIT:=true
  SORTED BY Dicom.InstanceNumber ORDER:=ascending SPLIT:=false;

selecting one or more View and Viewport Selection Parameters;

identifying View and Viewport Selection Rules based on the one or more View and Viewport Selection Parameters; and displaying the one or more images based on the Display Protocol Selection Rules, the Image Set Selection Rules and the View and Viewport Selection Rules.

In another further embodiment of the invention, a method of displaying images comprises the steps of:
  selecting one or more Study Selection Parameters;
  identifying Study Selection Rules based on the one or more Study Selection Parameters;
  receiving one or more images based on the Study Selection Rules;
  selecting one or more Display Protocol Selection Parameters based on the one or more images selected;
  identifying Display Protocol Selection Rules based on the one or more Display Protocol Selection Parameters;
  selecting one or more Image Set Selection Parameters;
  identifying Image Set Selection Rules based on the one or more Image Set Selection Parameters, where the Image Set Selection Rule is:
  IF (Dicom.Modality="CT" and Abstract.PriorIndex=0)
  THEN CREATE image set with ID 1.x
    SORTED BY Condition.CTSoftTisseKernel SPLIT:=true
    SORTED BY Dicom.SeriesNumber ORDER:=ascending SPLIT:=true
    SORTED BY Dicom.InstanceNumber ORDER:=ascending SPLIT:=false;
  selecting one or more View and Viewport Selection Parameters;
  identifying View and Viewport Selection Rules based on the one or more View and Viewport Selection Parameters; and
  displaying the one or more images based on the Display Protocol Selection Rules, the Image Set Selection Rules and the View and Viewport Selection Rules.

In an embodiment of the invention, a method of displaying images comprising the steps of:
  selecting one or more Study Selection Parameters;
  identifying Study Selection Rules based on the one or more Study Selection Parameters;
  receiving one or more images based on the Study Selection Rules;
  selecting one or more Display Protocol Selection Parameters based on the one or more images selected;
  identifying Display Protocol Selection Rules based on the one or more Display Protocol Selection Parameters;
  selecting one or more Image Set Selection Parameters;
  identifying an Image Set Selection Rule based on the one or more Image Set Selection Parameters, where the Image Set Selection Rule (Localizer) is:
  IF (Dicom.Modality="CT" and Condition.IsLocalizer=true)
  THEN CREATE image set with ID 1
    SORTED BY Dicom.SeriesNumber ORDER:=ascending SPLIT:=true
    SORTED BY Dicom.InstanceNumber ORDER:=ascending SPLIT:=false;
  selecting one or more View and Viewport Selection Parameters;
  identifying View and Viewport Selection Rules based on the one or more View and Viewport Selection Parameters; and
  displaying the one or more images based on the Display Protocol Selection Rules, the Image Set Selection Rules and the View and Viewport Selection Rules.

In a further embodiment of the invention, a method of displaying images comprising the steps of:
  selecting one or more Study Selection Parameters;
  identifying Study Selection Rules based on the one or more Study Selection Parameters;
  receiving one or more images based on the Study Selection Rules;
  selecting one or more Display Protocol Selection Parameters based on the one or more images selected;
  identifying Display Protocol Selection Rules based on the one or more Display Protocol Selection Parameters;
  selecting one or more Image Set Selection Parameters;
  identifying an Image Set Selection Rule based on the one or more Image Set Selection Parameters, where the Image Set Selection Rule (Localizer) is:
  IF (Dicom.Modality="CT" and Condition.IsLocalizer=true)
  THEN CREATE image set with ID 1
    SORTED BY Dicom.SeriesNumber ORDER:=ascending SPLIT:=true
    SORTED BY Dicom.InstanceNumber ORDER:=ascending SPLIT:=false;
  selecting one or more View and Viewport Selection Parameters;
  identifying View and Viewport Selection Rules based on the one or more View and Viewport Selection Parameters; and
  displaying the one or more images based on the Display Protocol Selection Rules, the Image Set Selection Rules and the View and Viewport Selection Rules.

In a still further embodiment of the invention, a method of displaying images comprising the steps of:
  selecting one or more Study Selection Parameters;
  identifying Study Selection Rules based on the one or more Study Selection Parameters;
  receiving one or more images based on the Study Selection Rules;
  selecting one or more Display Protocol Selection Parameters based on the one or more images selected;
  identifying Display Protocol Selection Rules based on the one or more Display Protocol Selection Parameters;
  selecting one or more Image Set Selection Parameters;
  identifying an Image Set Selection Rule based on the one or more Image Set Selection Parameters, where the Image Set Selection Rule (Localizer) is:
  IF (Dicom.Modality="CT" and Abstract.AlreadyReferenced=false)
  THEN CREATE image set with ID 2
    SORTED BY Dicom.SeriesNumber ORDER:=ascending SPLIT:=true
    SORTED BY Dicom.InstanceNumber ORDER:=ascending SPLIT:=false;
  selecting one or more View and Viewport Selection Parameters;
  identifying View and Viewport Selection Rules based on the one or more View and Viewport Selection Parameters; and
  displaying the one or more images based on the Display Protocol Selection Rules, the Image Set Selection Rules and the View and Viewport Selection Rules.

In a further embodiment of the invention, a method of displaying images comprising the steps of:
  selecting one or more Study Selection Parameters;
  identifying Study Selection Rules based on the one or more Study Selection Parameters;
  receiving one or more images based on the Study Selection Rules;
  selecting one or more Display Protocol Selection Parameters based on the one or more images selected;
  identifying Display Protocol Selection Rules based on the one or more Display Protocol Selection Parameters;
  selecting one or more Image Set Selection Parameters;

identifying an Image Set Selection Rule based on the one or more Image Set Selection Parameters, where the Image Set Selection Rule (Localizer) is:
IF (Dicom.Modality="CT" and Abstract.AlreadyReferenced=false)
THEN CREATE image set with ID 2
SORTED BY Dicom.SeriesNumber ORDER:=ascending SPLIT:=true
SORTED BY Dicom.InstanceNumber ORDER:=ascending SPLIT:=false;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected, where the one or more Display Protocol Selection Parameters include Viewer Assignment Rule:
IF (Abstract.ImageSetID=1)
THEN SELECT image set with score=10;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In an additional embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected, where the one or more Display Protocol Selection Parameters include Viewer Assignment Rule:
IF (Abstract.ImageSetID=1)
THEN SELECT image set with score=10;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In a further embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected, where the one or more Display Protocol Selection Parameters include Viewer Assignment Rule:
IF (Abstract.ImageSetID=2)
THEN SELECT image set with score=5;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In a still further embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters;
displaying the one or more images based on the Display Protocol Selection Rules, the Image Set Selection Rules and the View and Viewport Selection Rules; and
selecting Viewer Assignment Rule:
IF (Abstract.ImageSetID=2)
THEN SELECT image set with score=5.

In an embodiment of the invention, a method of displaying images comprising the steps of:
selecting one or more Study Selection Parameters;
identifying Study Selection Rules based on the one or more Study Selection Parameters, where the one or more Study Selection Rules comprise one or more Abstract Tags selected from the group consisting of:
(i) RelativeStudyAge indicates relative age of Study in days compared to primary Study.
(ii) PriorIndex indicates an index that enumerates all other studies from youngest to oldest.
(iii) NumImages indicates number of images in Study.

(iv) NumSeries indicated number of image series in Study.
(v) Num3DVolumes indicates number of 3D volumes in Study.
(vi) Num4DSequences indicates number of 4D sequences in Study (e.g. Cardiac CT).
(vii) HasReport indicates a flag that indicates if a report is available for a Study;

receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID.

In another embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements.

In a further embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements, where the Style Rule is:
IF (Abstract.DisplaySetID>100 and
Abstract.DisplaySetID<105 and
Dicom.Modality="PT")
THEN SET
RenderingStyle:="3D MIP"
Inverse:=true
DataWindow:="2% 98%".

In a still further embodiment of the invention, a method of displaying images comprising the steps of:

selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements, where the Style Rule is:
IF (Abstract.ImageSetID=200)
THEN SET
   RenderingStyle:="MPR"
   SliceThickness:="20"
   DataWindow:="DICOM1"
   ZoomFactor:="FitToWindow".

In an embodiment of the invention, a method of displaying one or more Sets of Images comprises the steps of:
selecting one or more Study Selection Parameters;
selecting or more Study Selection Rules based on the one or more Study Selection Parameters;
receiving one or more Sets of Images based on the Study Selection Rules;
selecting one or more Display Protocol Selection Parameters based on the one or more Sets of Images selected;
selecting one or more Display Protocol Selection Rules based on the one or more Display Protocol Selection Parameters; and
displaying the one or more Sets of Images based on the Display Protocol Selection Rules.

In a further embodiment of the invention, a method of displaying one or more Sets of Images comprises the steps of:
a. selecting a primary Study;
b. selecting one or more Study Selection Parameters based on the primary Study;
c. selecting one or more Study Selection Rules based on the one or more Study Selection Parameters;
d. selecting one or more Sets of Images from a plurality of images based on the one or more Study Selection Rules;
e. selecting one or more Display Protocol Selection Parameters based on the one or more Sets of Images selected;
f. selecting one or more Display Protocol Selection Rules based on the one or more Display Protocol Selection Parameters;
g. selecting one or more Display Parameters using the one or more Display Protocol Selection Rules, where the one or more Display Parameter are selected from the group consisting of Image Set Selection Parameters and View and Viewport Selection Parameters; and
h. displaying the one or more Sets of Images according to the Display Parameters.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one study from the plurality of Image Sets is a two dimensional image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one study from the plurality of Image Sets is a three dimensional (3D) image displayed with a 3D rendering style.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays an oblique cross section through a volumetric image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a maximum intensity projection of an image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a post processed rendering of an image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a thick slab image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a volume rendered image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a three dimensional image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where one or more Study Selection Rules used DICOM parameters and Abstract Tags derived from a single reference image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the primary Study selected is a single reference image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the primary Study selected is a single reference image, where one or more Study Selection Rules are derived from the single reference image DICOM Parameters.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Viewport Assignment Rules contain protocols for displaying two dimensional images in the one or more Viewports.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Abstract Tags are selected from the group consisting of RelativeStudyAge, PriorIndex. NumImages, NumSeries, Num3DVolumes, Num4DSequences and Has-Report.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Viewport Assignment Rules include one or more Abstract Tags selected from the group consisting of Image Sets to be displayed, Rendering Style, Additional image sets for image fusion, Image Alignment, Colormap/Transfer Function, Slice Thickness, Zoom Factor, Camera position, Camera orientation and Labels/Overlay elements.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Image Set Rules are selected from selection, sorting, and breaking rules, where the one or more Image Set Rules are Boolean expressions that contain parameters selected from the group consisting of DICOM parameters, abstract tags, and used-defined functions.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where in order to specify image sorting, the Image Set Rules contain an ordered list of sorting criteria.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where in order to specify image sorting, the Image Set Rules contain an ordered list of sorting criteria, where a split flag is used in order to specify image splitting.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where Abstract Tags are used in Image Set Rules.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where Abstract Tags are used in Image Set Rules, where an Abstract Tag identifies whether an image has already been placed into an Image Set.

In an alternative embodiment of the invention, a system of displaying one or more Sets of Images from a plurality of images comprises selecting one or more studies from a plurality of studies, one or more digital data processors for carrying out the steps including applying one or more Protocol Selection Rules to select a Display Protocol, where the one or more Protocol Selection Rules are based on one or more DICOM parameters and Abstract Tags from the plurality of studies, applying one or more Image Set Rules to define a plurality of Image Sets from the plurality of studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the one or more Image Sets based on one or more of the Protocol Selection Rules, the one or more Image Set Rules, the one or more Viewport Assignment Rules, and the one or more Style Rules, where at least one of the one or more Viewports displays a three dimensional image.

In another alternative embodiment of the invention, a method of displaying one or more Sets of Images from a plurality of images comprises selecting a primary Study from a plurality of studies, executing on a server digital data processor a render server program which applies one or more of one or more Study Selection Rules, one or more Protocol Selection Rule, one or more Image Set Rules, one or more Viewport Assignment Rules, and one or more Style Rules to display the one or more Sets of Images including the steps of applying the one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying the one or more Protocol Selection Rules to select a Display Protocol, where the one or more Protocol Selection Rules are based on one or more DICOM parameters and one or more Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the Protocol Selection Rule, the Image Set Rule, the one or more Viewport Assignment Rules, and the one or more Style Rules, where at least one of the one or more Viewports displays a volume rendered image.

In a further embodiment of the invention, a method of displaying one or more Sets of Images from a plurality of images comprises selecting a primary Study from a plurality of studies, executing on a server digital data processor a render server program which applies one or more of one or more Study selection Rules, one or more Protocol Selection Rules, one or more Image Set Rules, one or more Viewport Assignment Rules, and one or more Style Rules to display the one or more Sets of Images including the steps of applying the one or more Study Selection Rules to generate a plurality of second studies based on DICOM parameter BodyPartExamined, DICOM parameter Modality, DICOM parameter RelativeStudyAge and Abstract Tag RelativeStudyAge, Abstract Tag PriorIndex, Abstract Tag NumImages, Abstract Tag NumSeries, Abstract Tag Num3DVolumes, Abstract Tag Num4DSequences and Abstract Tag HasReport from the plurality of studies, where the plurality of second studies include the primary Study, applying the one or more Protocol Selection Rules to select a Display Protocol, where the one or more Protocol Selection Rules are based on DICOM parameter BodyPartExamined, DICOM parameter Modality, DICOM parameter HasThisSliceVolumes, DICOM parameter StudyDescription and Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the one or more Protocol Selection Rules, the one or more Image Set Rules, the one or more Viewport Assignment Rules, and the one or more Style Rules, where at least one of the one or more Viewports displays a post processed rendering of an image set.

In a further embodiment of the invention, a method of displaying one or more Sets of Images from a plurality of images comprises selecting a primary Study from a plurality of studies, executing on a server digital data processor a render server program which applies one or more of one or more Study selection Rules, one or more Protocol Selection Rules, one or more Image Set Rules, one or more Viewport Assignment Rules, and one or more Style Rules to display the one or more Sets of Images including the steps of applying the one or more Study Selection Rules to generate a plurality of second studies based on DICOM parameter BodyPartExamined, DICOM parameter Modality, DICOM parameter RelativeStudyAge and Abstract Tag RelativeStudyAge, Abstract Tag PriorIndex, Abstract Tag NumImages, Abstract Tag NumSeries, Abstract Tag Num3DVolumes, Abstract Tag Num4DSequences and Abstract Tag HasReport from the plurality of studies, where the plurality of second studies include the primary Study, applying the one or more Protocol Selection Rules to select a Display Protocol, where the one or more Protocol Selection Rules are based on DICOM parameter BodyPartExamined, DICOM parameter Modality, DICOM parameter HasThisSliceVolumes, DICOM parameter StudyDescription and Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the one or more Protocol Selection Rules, the one or more Image Set Rules, the one or more Viewport Assignment Rules, and the one or more Style Rules, where at least one of the one or more Viewports displays a post processed rendering of an image set, where the step of displaying is carried out on a client display device.

In an embodiment of the present invention, a method comprises providing a server computer having a plurality of medical diagnostic reports stored thereon, where the plurality of medical diagnostic reports can be accessed based on a plurality of patient IDs, the server receiving a user ID and a patient ID, the server displaying one or more medical diagnostic reports selected from the plurality of medical diagnostic reports accessible by the user ID and corresponding to the patient ID, the server receiving a selection comprising one or more reports selected from the one or more medical diagnostic reports displayed, the server executing a server program which retrieves one or more phis of metadata for the selection, the server program computes one or more concatenated values for the one or more phis of metadata and the server program computing one or more secure values for the one or more concatenated values using a secure hash function and one or both the server and the server program exporting the selection, where the one or more secure values are substituted for the one or more phis of metadata.

In an embodiment of the present invention, a method comprises providing a server computer having a plurality of medical diagnostic reports stored thereon, where the plurality of medical diagnostic reports can be accessed based on a plurality of patient IDs, the server receiving a user ID and a patient ID, the server displaying one or more medical diagnostic reports selected from the plurality of medical diagnostic reports accessible by the user ID and corresponding to the patient ID, the server receiving a selection comprising one or more reports selected from the one or more medical diagnostic reports displayed, the server executing a server program which retrieves one or more phis of metadata for the selection, the server program computes one or more concatenated values for the one or more phis of metadata and the server program computing one or more secure values for the one or more concatenated values using a secure hash function, where the secure hash function is selected from the group consisting of MD4, MD5, SHA-1, SHA-2, Skein, and BLAKE, and one or both the server and the server program exporting the selection, where the one or more secure values are substituted for the one or more phis of metadata.

In an embodiment of the present invention, a method comprises providing a server computer having a plurality of medical diagnostic reports stored thereon, where the plurality of medical diagnostic reports can be accessed based on a plurality of patient IDs, the server receiving a user ID and a patient ID, the server displaying one or more medical diagnostic reports selected from the plurality of medical diagnostic reports accessible by the user ID and corresponding to the patient ID, the server receiving a selection comprising one or more reports selected from the one or more medical diagnostic reports displayed, the server executing a server program which retrieves one or more phis of metadata for the selection, the server program computes one or more concatenated values for the one or more phis of metadata, where a separator character is used to concatenate the one or more phis of metadata and the server program computing one or more secure values for the one or more concatenated values using a secure hash function and one or both the server and the server program exporting the selection, where the one or more secure values are substituted for the one or more phis of metadata.

In an embodiment of the present invention, a method comprises providing a server computer having a plurality of medical diagnostic reports stored thereon, where the plurality of medical diagnostic reports can be accessed based on a plurality of patient IDs, the server receiving a user ID and a patient ID, the server displaying one or more medical diagnostic reports selected from the plurality of medical diagnostic reports accessible by the user ID and corresponding to the patient ID, the server receiving a selection comprising one or more reports selected from the one or more medical diagnostic reports displayed, the server executing a server program which retrieves one or more phis of metadata for the selection, the server program computes one or more concatenated values for the one or more phis of metadata and the server program computing one or more secure values for the one or more concatenated values using a secure hash function, where the server program adds an institution aware ID to the one or more secure values and one or both the server and the server program export the selection, where the one or more secure values are substituted for the one or more phis of metadata.

In an embodiment of the present invention, a method comprises providing a display device to display one or more medical diagnostic reports, the display device including a display device memory and a display device processor in communication with a server, receiving a user ID and a patient ID, displaying a plurality of medical diagnostic reports, identifying and receiving one or more medical diagnostic reports from the plurality of medical diagnostic reports displayed, where one or more phis of metadata in the one or more medical diagnostic reports are substituted for one or more secure values, where the one or more secure values are computed from one or more concatenated values using a secure hash function selected from the group consisting of MD4, MD5, SHA-1, SHA-2, Skein, and BLAKE, and the one or more concatenated values are computed from one or more phis of metadata in the selection stored on the server and displaying the one or more medical diagnostic reports.

In an embodiment of the present invention, a method comprises providing a display device to display one or more medical diagnostic reports, the display device including a display device memory and a display device processor in communication with a server, receiving a user ID and a patient ID, displaying a plurality of medical diagnostic reports, identifying and receiving one or more medical diagnostic reports from the plurality of medical diagnostic reports displayed, where one or more phis of metadata in the one or more medical diagnostic reports are substituted for one or more secure values, where the one or more secure values are computed from one or more concatenated values using a secure hash function selected from the group consisting of MD4, MD5, SHA-1, SHA-2, Skein, and BLAKE, and the one or more concatenated values are computed from one or more phis of metadata in the selection stored on the server and displaying the one or more medical diagnostic reports, where a first secure value displayed corresponding to a first phi of metadata in a first medical report is the same as a second secure value corresponding to a second phi of metadata displayed in a second medical report when the first phi of metadata is the same as the second phi of metadata.

In an embodiment of the present invention, a method comprises providing a display device to display one or more medical diagnostic reports, the display device including a display device memory and a display device processor in communication with a server, receiving a user ID and a patient ID, displaying a plurality of medical diagnostic reports, identifying and receiving one or more medical diagnostic reports from the plurality of medical diagnostic reports displayed, where one or more phis of metadata in the one or more medical diagnostic reports are substituted for one or more secure values, where the one or more secure values are computed from one or more concatenated values using a secure hash function selected from the group consisting of MD4, MD5, SHA-1, SHA-2, Skein, and BLAKE, and the one or more concatenated values are computed from one or more phis of metadata in the selection stored on the server and displaying the one or more medical diagnostic reports, where the one or more secure values are not stored on the display device memory.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents. The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

Embodiments contemplated herein further include Embodiments S1-S20 following.

Embodiment S1. An embodiment of the invention, a method comprising providing a server computer having a plurality of medical diagnostic reports stored thereon, where one or more medical diagnostic reports can be accessed based on one or both a user ID and a patient ID; the server, receiving the user ID and the patient ID, displaying a listing of the one or more medical diagnostic reports selected from the plurality of medical diagnostic reports accessible by the user ID and corresponding to the patient ID, receiving a selection comprising one or more reports selected from the one or more medical diagnostic reports displayed, executing a server program which applies one or more of one or more Study Selection Rules based on the user ID and the patient ID to the selection to retrieve one or more phis of metadata containing protected health information in the selection, adds an institution aware ID to the one or more phis of metadata to generate one or more combined values, concatenates the one or more combined values to generate one or more concatenated value using a separator character, where the separator character is not included in the one or more phis of metadata, and computes one or more secure values from the one or more concatenated values using a secure hash function selected from the group consisting of MD4, MD5, SHA-1, SHA-2, Skein, and BLAKE, and displaying to a remote computer the selection, where the one or more secure values are substituted for the one or more phis of metadata.

Embodiment S2. The method of embodiment S1, where a first secure value displayed corresponding to a first phi of metadata in a first medical report is the same as a second secure value corresponding to a second phi of metadata displayed in a second medical report when the first phi of metadata is the same as the second phi of metadata.

Embodiment S3. The method of embodiment S1, where the one or more secure values are not stored on the remote computer.

Embodiment S4. The method of embodiment S1, where the one or more secure values displayed cannot be used to generate the one or more phis of metadata.

Embodiment S5. An embodiment of the invention, a method comprising providing a server computer having a plurality of medical diagnostic reports stored thereon, where the plurality of medical diagnostic reports can be accessed based on a plurality of patient IDs, the server, receiving a user ID and a patient ID, displaying one or more medical diagnostic reports selected from the plurality of medical diagnostic reports accessible by the user ID and corresponding to the patient ID, receiving a selection comprising one or more reports selected from the one or more medical diagnostic reports displayed, executing a server program which, receives the selection, computes one or more concatenated values for one or more phis of metadata in the selection, computes one or more secure values for the one or more concatenated values using a secure hash function selected from the group consisting of MD4, MD5, SHA-1, SHA-2, Skein, and BLAKE; and substitute the one or more secure values for the one or more phis of metadata in the selection, and exporting the selection to a client.

Embodiment S6. The method of embodiment S5, where the one or more secure values displayed cannot be used to generate the one or more phis of metadata.

Embodiment S7. The method of embodiment S5, where the first secure value and the second secure value are stored on the server and not stored on the client.

Embodiment S8. The method of embodiment S5, where a first secure value displayed corresponding to a first phi of metadata in a first medical report is the same as a second secure value corresponding to a second phi of metadata displayed in a second medical report when the first phi of metadata is the same as the second phi of metadata.

Embodiment S9. The method of embodiment S8, where the first phi of metadata and the second phi of metadata are stored on the server and not stored on the client.

Embodiment S10. The method of embodiment S5, further comprising adding an institution aware ID to the one or more secure values.

Embodiment S11. The method of embodiment S5, further using a separator character in step iv) 2) to compute the one or more phis of metadata.

Embodiment S12. An embodiment of the invention, a method comprising providing a display device to display one or more medical diagnostic reports, the display device including a display device memory and a display device processor in communication with a server, receiving a user ID and a patient ID, communicating the user ID and the patient ID to the server, displaying a plurality of medical diagnostic reports accessible by the user ID and corresponding to the patient ID, receiving a selection comprising one or more medical diagnostic reports from the plurality of medical diagnostic reports displayed, and displaying the selection, where one or more phis of metadata in the selection stored on the server are substituted for one or more secure values, where the one or more secure values are computed from one or more concatenated values using a secure hash function selected from the group consisting of MD4, MD5, SHA-1, SHA-2, Skein, and BLAKE, and the one or more concatenated values are computed from one or more phis of metadata in the selection stored on the server.

Embodiment S13. The method of embodiment S12, where a first secure value displayed corresponding to a first phi of metadata in a first medical report is the same as a second secure value corresponding to a second phi of metadata displayed in a second medical report when the first phi of metadata is the same as the second phi of metadata.

Embodiment S14. The method of embodiment S12, where the one or more secure values are not stored on the display device memory.

Embodiment S15. The method of embodiment S12, where the one or more secure values displayed cannot be used to generate the one or more phis of metadata.

Embodiment S16. The method of embodiment S12, where a first secure value displayed corresponding to a first phi of metadata in a first medical report is the same as a second secure value corresponding to a second phi of metadata displayed in a second medical report when the first phi of metadata is the same as the second phi of metadata.

Embodiment S17. The method of embodiment S16, where the first secure value and the second secure value stored on the server are not stored on the display device memory.

Embodiment S18. The method of embodiment S16, where the first phi of metadata and the second phi of metadata stored on the server are not stored on the display device memory.

Embodiment S19. The method of embodiment S12, further comprising in step e) adding an institution aware ID to the one or more secure values.

Embodiment S20. The method of embodiment S12, further comprising in step e) using a separator character to compute the one or more concatenated values from the one or more phis of metadata.

What is claimed:

1. A method of accessing a library of medical diagnostic reports, where each medical diagnostic report comprises an image with Protected Health Information (PHI) overlaid on the image, where a server executes a server program which carries out the steps comprising:
   1) receiving a patient ID and a user ID from a user through a remote computer;
   2) sending a dialog box to the remote computer, where the dialog box comprises one or more options to configure two or more Study Selection Rules, where a Study Selection Rule of the two or more Study Selection Rules is an option to de-identify PHI;
   3) receiving a response to the dialog box from the remote computer, where the response configures the two or more Study Selection Rules, where the option to de-identify is configured in the Study Selection Rule;
   4) retrieving one or more phis of metadata containing PHI from a first list based on the two or more Study Selection Rules, where the first list comprises a plurality of medical diagnostic reports accessible by the user ID and where the first list comprises a plurality of medical diagnostic reports of the patient ID;
   5) computing one or more secure values from the one or more phis of metadata;
   6) sending the first list to the remote computer;
   7) receiving from the remote computer a second list comprising one or more medical diagnostic reports, where the second list is selected from the first list; and
   8) sending one or more medical diagnostic reports from the second list to the remote computer, where the one or more medical diagnostic reports comprise an image with the one or more secure values overlaid on the image.

2. The method of claim 1, where a first secure value displayed corresponding to a first phi of metadata in a first medical report is the same as a second secure value corresponding to a second phi of metadata displayed in a second medical report when the first phi of metadata is the same as the second phi of metadata.

3. The method of claim 1, where the one or more secure values are not stored on the remote computer.

4. The method of claim 1, where a second Study Selection Rule of the two or more Study Selection Rules generates the first list, where the second Study Selection Rule comprises a pseudo code:
   "IF (Primary.Dicom.BodyPartExamined) is 'ANATOMICAL REGION 1' and (Primary.Dicom.Modality='IMAGE TYPE 1'), THEN SELECT (Other.Dicom.BodyPartExamined='ANATOMICAL REGION 1' and Other.Dicom.Modality='IMAGE TYPE 2')",
   where IMAGE TYPE 1 is not equal to IMAGE TYPE 2.

5. A method of accessing a library of medical diagnostic reports, where each medical diagnostic report comprises an image with Protected Health Information (PHI) overlaid on the image, where a server executes a server program carrying out the steps comprising:
   i) receiving a patient ID and a user ID from a user through a remote computer;
   ii) sending a dialog box to the remote computer, where the dialog box comprises two or more options to configure two or more Study Selection Rules, where a Study Selection Rule of the two or more Study Selection Rules is an option to de-identify PHI;
   iii) receiving a response to the dialog box from the remote computer, where the response configures the two or more Study Selection Rules, where the option to de-identify is configured in the Study Selection Rule;
   iv) displaying on the remote computer a first list, where the first list comprises a plurality of medical diagnostic reports accessible by the user ID and where the first list comprises a plurality of medical diagnostic reports of the patient ID;
   v) receiving from the remote computer a second list comprising one or more medical diagnostic reports, where the second list is selected from the first list based on the two or more Study Selection Rules;
   vi) retrieving one or more phis of metadata containing protected health information from the one or more medical diagnostic reports in the second list based on the Study Selection Rule;
   vii) computing one or more secure values for the one or more phis of metadata;
   viii) substituting the one or more secure values for the one or more phis of metadata in the one or more medical diagnostic reports comprising the second list; and
   ix) exporting to the remote computer the one or more medical diagnostic reports from the second list, where the one or more medical diagnostic reports comprise the image with the one or more secure values overlaid on the image.

6. The method of claim 5, where the one or more secure values displayed cannot be used to generate the one or more phis of metadata.

7. The method of claim 5, where a first secure value displayed corresponding to a first phi of metadata in a first medical report is the same as a second secure value corresponding to a second phi of metadata displayed in a second medical report when the first phi of metadata is the same as the second phi of metadata.

8. The method of claim 7, where the first phi of metadata and the second phi of metadata are not stored on the remote computer.

9. The method of claim 5, where a second Study Selection Rule of the two or more Study Selection Rules generates the first list, where the second Study Selection Rule comprises a pseudo code:
   "IF (Primary.Dicom.BodyPartExamined) is 'ANATOMICAL REGION 1' and (Primary.Dicom.Modality='IMAGE TYPE 1'), THEN SELECT (Other.Dicom.BodyPartExamined='ANATOMICAL REGION 1' and Other.Dicom.Modality='IMAGE TYPE 2')",
   where IMAGE TYPE 1 is not equal to IMAGE TYPE 2.

10. The method of claim 5, further comprising adding an institution aware ID to generate the one or more secure values.

11. The method of claim 5, further comprising adding a separator character to generate the one or more secure values.

12. A method of accessing on a display device a library of medical diagnostic reports, where each medical diagnostic report comprises an image with Protected Health Information (PHI) overlaid on the image, the display device comprising a display device memory and a display device processor in communication with a server, the display device carrying out the steps comprising,
   a) receiving a patient ID and a user ID from a user;
   b) communicating the user ID and the patient ID to the server;
   c) displaying a dialog box, where the dialog box comprises two or more options to configure two or more Study Selection Rules, where a Study Selection Rule of the two or more Study Selection Rules is an option to de-identify PHI;
   d) sending a response to the dialog box to the server, where the response configures the two or more Study Selection Rules, where the option to de-identify is configured in the Study Selection Rule;
   e) receiving a first list from the server, where the first list comprises a plurality of medical diagnostic reports accessible by the user ID and where the first list comprises a plurality of medical diagnostic reports of the patient ID, where one or more secure values are substituted for one or more phis of metadata containing PHI from the plurality of medical diagnostic reports in the first list based on the two or more Study Selection Rules;
   f) sending a second list to the server, where the second list comprises one or more medical diagnostic reports selected from the first list; and
   g) displaying a first image with the one or more secure values overlaid on the first image of the one or more medical diagnostic reports in the second list.

13. The method of claim 12, where the one or more phis of metadata are not transmitted to the display device.

14. The method of claim 12, where the one or more secure values displayed cannot be used to generate the one or more phis of metadata.

15. The method of claim 12, where a second Study Selection Rule of the two or more Study Selection Rules generates the first list, where the second Study Selection Rule comprises a pseudo code:
   "IF (Primary.Dicom.BodyPartExamined) is 'ANATOMICAL REGION 1' and (Primary.Dicom.Modality='IMAGE TYPE 1'), THEN SELECT (Other.Dicom.BodyPartExamined='ANATOMICAL REGION 1' and Other.Dicom.Modality='IMAGE TYPE 2')",
   where IMAGE TYPE 1 is not equal to IMAGE TYPE 2.

16. The method of claim 12, where a first secure value displayed corresponding to a first phi of metadata in a first medical report is the same as a second secure value corresponding to a second phi of metadata displayed in a second medical report when the first phi of metadata is the same as the second phi of metadata.

17. The method of claim 16, where the first secure value and the second secure value are stored on the server.

18. The method of claim 16, where the first phi of metadata and the second phi of metadata stored on the server are not stored on the display device memory.

19. The method of claim 12, further comprising adding an institution aware ID to generate the one or more secure values.

20. The method of claim 12, further comprising adding a separator character to generate the one or more secure values.

* * * * *